US008012465B2

(12) United States Patent
Elias et al.

(10) Patent No.: US 8,012,465 B2
(45) Date of Patent: Sep. 6, 2011

(54) METHODS FOR TREATING RENAL CELL CARCINOMA

(75) Inventors: Laurence Elias, Emeryville, CA (US); Gary Witherell, Emeryville, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

(21) Appl. No.: 12/460,991

(22) Filed: Jul. 28, 2009

(65) Prior Publication Data

US 2010/0316595 A1     Dec. 16, 2010

Related U.S. Application Data

(63) Continuation of application No. 11/342,243, filed on Jan. 27, 2006, now abandoned.

(60) Provisional application No. 60/647,496, filed on Jan. 27, 2005.

(51) Int. Cl.
*A61K 38/16* (2006.01)
*A61K 38/20* (2006.01)

(52) U.S. Cl. ............... 424/85.2; 424/85.1; 514/19.2; 514/19.3

(58) Field of Classification Search .............. None
See application file for complete search history.

(56) References Cited

U.S. PATENT DOCUMENTS

| 4,752,585 A | * | 6/1988 | Koths et al. | ............ | 435/252.33 |
| 4,766,106 A | | 8/1988 | Katre et al. | | |
| 4,931,543 A | | 6/1990 | Halenbeck et al. | | |
| 5,830,452 A | * | 11/1998 | Bauer et al. | ............ | 424/85.2 |

FOREIGN PATENT DOCUMENTS

WO    WO 2004/002526 A1    1/2004

OTHER PUBLICATIONS

Nieken et al., 1992, J. Clin. Oncol. 10:1119-1123.*
Amato, et al., "Phase II Study of Thalidomide + Interleukin-2 (IL-2) In Patients With Metastic Renal Cell Carcinoma (MRCC)," *Proc Am Soc Clin Oncol 22*:Abstract #1556 (2003).
Angevin, et al., "Phase 1 Study of Prolonged Low-Dose Subcutanceous Recombinant Interleukin-2 (IL-2) In Patients With Advanced Cancer," *J Immunol 18*(3):188-195 (1995)
Atzpodian, et al., "Low-Dose Subcutaneous Recombinant Interleukin-2 In Advanced Human Malignancy: A Phase II Outpatient Study," *Mol Biother 2*:18-26 (1990).
Bordin, et al., "Five-Year Survival Results of Subcutaneous Low-Dose Immunotherapy With Interleukin-2 Alone in Metastic Renal Cell Cancer Patients," *Urol Int 64*:3-8 (2000).
Buter, et al., "A Progress Report on the Outpatient Treatment of Patients With Advanced Renal Cell Carcinoma Using Subcutaneous Interleukin-2," *Semin Oncol 20*(6):61 (1993).
De Lena, et al., "Subcutaneous rIL-2 in Advanced Melanoma and Kidney Carcinoma," *Int J Oncology 1*:181-189 (1992).

Duggan, et al., "A Phase II Study of Recombinant Interleukin-2 With or Without Recombinant Interferon-Beta in Non-Hodgkin's Lymphoma. A Study of the Cancer and Leukemia Group B,"*J Immunother 12*:115-122 (1992).
Fumagalli, et al., "Pretreatment of Serum Markers and Lymphocyte Response to Interleukin-2 Therapy" *Br J Cancer 80*(3/4):407-411 (1999).
Guida, et al., "Long-Term Subcutaneous Recombinant Interleukkin-2 As Maintenance Therapy: Biological Effects and Clinical Implications," *Cancer Biother 10*(3):195-203 (1995).
Jayson, et al., "A Randomized Phase II Trial of Interleukin 2 and Interleukin 2-Interferon Alpha in Advanced Renal Cancer," Br J Cancer 78(3):366-369 (1998).
Leahy, et al., "Phase I Study Comparing Continuous Infusion of Recombinant Interleukin-2 by Subcutaneous or Intravenous Administration," *Eur J Cancer 28A*(6/7):1049-1051 (1992).
Lissoni, et al., "Abrogation of the Negative Influence of Opoids on IL-2 Immunotherapy of Renal Cell Cancer by Melatonin," *European Urology 38*:115-118 (2000).
Lissoni, et al., "In Vivo Stimulation of IL-2 Secretion by Subcutaneous Low-Dose IL-2 in Metastic Cancer Patients," *Br J Cancer 77*(11):1957-1960 (1998).
Lissoni, et al., "Prognostic Factors of the Clinical Response to Subcutaneous Immunotherapy With Interleukin-2 Alone in Patients With Metastatic Renal Cell Carcinoma," *Oncology 51*:59-62 (1994).
Lissoni, et al., "Vascular Endothelial Growth Factor (VEGF) Serum Levels During Cancer Immunotherapy With Il-2: Preliminary Considerations" *Int J Biol Markers 13 (2)*:98-101 (1998).
Lissoni, et al., "Second Line Therapy With Low-Dose Subcutaneous Interleukin-2 Alone in Advanced Renal Cancer Patients Resistant to Interferon Alpha," *Eur J Cancer 28 (1)*:92-96 (1992).
Lissoni, et al., "A Randomized Study of Low-Dose Interleukin-2 Subcutaneous Immunotherapy Versus Interleukin-2 Plus Interferon-Alpha As First Line Therapy for Metastic Renal Cell Carcinoma," *Tumori 79*:397-400 (1993).
Lissoni, et at, "Ten-Year Survival Results in Metastatic Renal Cell Cancer Patients Treated With Monoimmunotherapy With Subcutaneous Low-Dose Interleukin-2," *Anticancer Research 22*:1061-1064 (2002).
Lissoni, et al., "Clinical and Biological Effects of Interleukin-2 With or Without a Concomitant Administration of Granulocyte-Macrophage Colony-Stimulating Factor in Metastatic Cancer Patients," in Vivo 17:73-76 (2003).
Hannigen, et at., "Interleukin-2 Based Home Therapy of Metastatic Renal Cell Carcinoma: Risks and Benefits in 215 Consecutive Institution Patients," *J Urology 155*:19-25 (1996).
Nagler, et at, "The Effect of Low-Dose Interleukin-2 Based Immunotherapy on Salivary Function and Composition in Patients With Metastic Renal Cell Carcinoma," *Archives Oral Bio 46*:487-493 (2001).

(Continued)

*Primary Examiner* — Elizabeth C Kemmerer
(74) *Attorney, Agent, or Firm* — Robins & Pasternak LLP

(57) ABSTRACT

Methods for treating renal cell carcinoma using low doses of IL-2 are disclosed. In particular, the invention relates to methods of treating metastatic renal cell carcinoma in patients who are renally impaired and/or intolerant of high dose IL-2 therapy. The therapeutic regimen described herein significantly inhibits tumor growth with reduced toxicity and adverse side effects compared to high dose IL-2 therapy.

18 Claims, 5 Drawing Sheets

OTHER PUBLICATIONS

Nieken, et al., "Outpatient-Based Subcutaneous Interleukin-2 Monotherapy in Advanced Renal Cell Carcinoma: An Update," *Cancer Biotherapy and Radiopharmacoceuticals* 11(5):289-295 (1996).

Rosenburg, et al., "Use of Tumor-Infiltrating Lymphocytes and Interleukin-2 in the Immunotherapy of Patients With Metastic Melanoma," *N Engl J Med 319*:1676-1680 (1988).

Rosenburg, et at., The Development of New Immunotherapies for the Treatment of Cancer Using Interleukin-2, *Annals of Surg 208*(2):121-135 (1988).

Schiller, et al., "A Direct Comparison of Immunological and Clinical Effects of Interleeukin-2 With and Without Interferon-Alpha in Humans," *Cancer Res 53*:1286-1292 (1993).

Schomburg, et at, "Renal, Metabolic, and Hemodynamic Side-Effects of Interleukin-2 and/or Interferon Alpha: Evidence of a Risk/ Benefit Advantage of Subcutaneous Therapy," *J Cancer Res Clin Incol 119*:745-755 (1993).

Sleijfer, et al., "Phase II Study of Subcutaneous Interleukin-2 in Unselected Patients With Advanced Renal Cell Cancer of an Outpatient Basis," *J Clin Oncol 10*(7):1119-1123 (1992).

Stein, et al., "The Clinical Effects of Prolonged Treatment of Patients With Advanced Cancer With Low-Dose Subcutaneous Interleukin-2," *Br J Cancer 63*:275-278 (1991).

Tagliaferri, et al., "Daily Low-Dose Subcutaneous Recombinant Interleukin-2 by Alternate Weekly Administration: Antitumor Activity and Immunomodulatory Effects," *Am J Clin Oncol 21*(1):48-53 (1998).

Topalian, et al., "Immunotherapy of Patients With Advanced Cancer Using Tumor-Infiltrating Lymphocytes and Recombinant Interleukin-2: a Pilot Study," *J Clin Oncol 6*(5):839-853 (1988).

Tourani, et al., "Outpatient Treatment With Subcutaneous Interleukin-2 and Interferon Alfa Administration in Combination With Fluorouracil in Patients With Metastatic Renal Cell Carcinoma: Results of a Sequential Nonrandomized Phase II Study," *J Clin Oncol 16*(7):2505-2513 (1998).

Tourani, et al., "Subcutaneous Recombinant Interleukin-2 (rIL-2) in Outpatients With Metastic Renal Cell Carcinoma," *Annals Oncol 7*:525-528 (1996).

Verra, et al., "Immunotherapy With Concurrent Subcutaneous Gm-Csf, Low Dose IL-2 and IFN-Alpha in Patients With Progressive Metastic Renal Cell Carcinoma," *Br J Cancer 88*:1346-1351 (2003).

Whitehead, et al., "Subcutaneous Recombinant Interleukin-2 in a Dose Escalating Regimen in Patients With Metastatic Renal Cell Adenocarcinoma," *Cancer Research 50*:6708-6715 (1990).

\* cited by examiner

METHODS FOR TREATING RENAL CELL CARCINOMA

CROSS-REFERENCE TO RELATED APPLICATION

This application is a continuation of U.S. application Ser. No. 11/342,243, filed Jan. 27, 2006, now abandoned, from which priority is claimed pursuant to 35 U.S.C. §120, which application claims the benefit under 35 U.S.C. §119(e)(1) of provisional application 60/647,496, filed Jan. 27, 2005, which applications are hereby incorporated by reference in their entireties.

TECHNICAL FIELD

The present invention pertains generally to methods for treating renal cell carcinoma with IL-2. In particular, the invention relates to methods of treating renal cell carcinoma in patients who are renally impaired or intolerant of high-dose IL-2 therapy.

BACKGROUND

Interleukin-2 (IL-2) is a potent stimulator of natural killer (NK) and T-cell proliferation and function (Morgan et al. (1976) *Science* 193:1007-1011). This naturally occurring lymphokine has been shown to have anti-tumor activity against a variety of malignancies either alone or when combined with lymphokine-activated killer (LAK) cells or tumor-infiltrating lymphocytes (TIL) (see, for example, Rosenberg et al., *N. Engl. J. Med.* (1987) 316:889-897; Rosenberg, *Ann. Surg.* (1988) 208:121-135; Topalian et al., *J. Clin. Oncol.* (1988) 6:839-853; Rosenberg et al., *N. Engl. J. Med.* (1988) 319:1676-1680; and Weber et al., *J. Clin. Oncol.* (1992) 10:33-40). The anti-tumor activity of IL-2 has best been described in patients with metastatic melanoma and renal cell carcinoma using Proleukin®, a commercially available IL-2 formulation from Chiron Corporation, Emeryville, Calif. Other diseases, including lymphoma, also appear to respond to treatment with IL-2 (Gisselbrecht et al., *Blood* (1994) 83:2020-2022). However, high doses of IL-2 used to achieve positive therapeutic results with respect to tumor growth frequently cause severe side effects, including fever and chills, hypotension and capillary leak (vascular leak syndrome or VLS), and neurological changes (see, for example, Duggan et al., *J. Immunotherapy* (1992) 12:115-122; Gisselbrecht et al., *Blood* (1994) 83:2081-2085; and Sznol and Parkinson, *Blood* (1994) 83:2020-2022).

Metastatic renal cell carcinoma (RCC) is generally resistant to chemotherapy, either with single agents or with multiple agents in combination. Greater success has been seen with immunotherapy, particularly with the use of IL-2. Therapy with high dose intravenous IL-2 has resulted in objective tumor responses in approximately 15% of patients, some with long durability. However, the administration of high dose IL-2 is associated with capillary leak syndrome, which results in hypotension and reduced organ perfusion, which can be severe and sometimes fatal. These toxicities have generally restricted the use of IL-2 to a highly selected group of patients administered by physicians with significant experience in its administration. The use of lower-dose and subcutaneously administered regimens of IL-2 alone or in combination with other biologic agents, such as interferon-α, has been explored in an effort to develop a more broadly applicable therapy for this disease (see, for example, Nieken et al., *Cancer Biother. Radiopharm.* (1996) 11:289-295; Sleijfer et al., *J. Clin. Oncol.* (1992) 10:1119-1123; Lessoni et al., *Anticancer Res.* (2002) 22:1061-1-1064; Tourani et al., *J. Clin. Oncol.* (1998) 16:2505; and Schiller et al. *Cancer Res.* (1993) 53:1286-1292).

There remains a need for an improved therapy for treating patients having renal cell carcinoma that would reduce toxicity and improve therapeutic efficacy.

SUMMARY OF THE INVENTION

The present invention provides an efficacious method for treating renal cell carcinoma with IL-2. The method utilizes a relatively low dose of IL-2 compared to dosages used previously in high dose IL-2 therapies in order to reduce toxicity. As shown in the examples herein, this therapeutic regimen significantly inhibits tumor growth with reduced adverse side effects and provides an alternative treatment for patients who cannot tolerate high dose IL-2 therapy.

In one aspect, the invention provides a method for treating a human patient having renal cell carcinoma. In certain embodiments, the patient is renally impaired. In certain embodiments, the renal cell carcinoma is metastatic. In certain embodiments, the patient is intolerant of high dose IL-2 treatment.

In one embodiment, the method comprises: a) administering a dose of 1-52 MIU of IL-2 per day, in 1-3 doses a day, for 3-6 days a week, repeated for 1-24 weeks; and b) administering no IL-2 for 1-4 weeks.

In another embodiment, the method comprises: a) administering a dose of 1-52 MIU of IL-2 every 5 days to 1 month, repeated for 1-24 weeks, wherein the IL-2 is covalently conjugated to polyethylene glycol or polyoxyethylated polyol; and b) administering no IL-2 for 1-4 weeks.

In a further embodiment, the method comprises: a) administering a dose of 9-18 MIU of IL-2 per day, in 1-3 doses a day, for 3-6 days a week, repeated for 1-24 weeks; b) administering no IL-2 for 1-4 weeks; c) administering a dose of 9 MIU of IL-2 per day, in 1-3 doses a day, for 3-6 days a week, repeated for 1-24 weeks; and d) administering no IL-2 for 1-4 weeks.

In yet another embodiment, the method comprises: a) first, administering a dose of 18 MIU of IL-2 per day for 5 days during one week; b) second, administering a dose of 9 MIU of IL-2 per day for 2 days followed by administering a dose of 18 MIU of IL-2 per day for 3 days during each week, repeated for 5 weeks; c) third, administering no IL-2 for 3 weeks; d) fourth, administering a dose of 9 MIU of IL-2 per day for 5 days of each week, repeated for 6 weeks; and e) fifth, administering no IL-2 for 3 weeks.

In any of the methods described herein, the IL-2 can be recombinantly produced IL-2. The IL-2 can include human IL-2 or variants thereof comprising a sequence having at least about 70-100% sequence identity to the sequence of human IL-2 (SEQ ID NO:1), including any percent identity within these ranges, such as 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% sequence identity thereto. In certain embodiments, the IL-2 is an IL-2 mutein, for example, but not limited to, $Ala_{104}$ $Ser_{125}$ IL-2; des-$Ala_1$ des-$Pro_2$ des-$Thr_3$ des-$Ser_4$ $Ala_{104}$ $Ser_{125}$ IL-2; and des-$Ala_1$ des-$Pro_2$ des-$Thr_3$ des-$Ser_4$ des-$Ser_5$ des-$Ser_6$ IL-2. In a preferred embodiment, the IL-2 mutein is des-alanyl-1, serine-125 human interleukin-2 (aldesleukin).

In certain embodiments, the IL-2 is conjugated to a polyethylene glycol. Exemplary polyethylene glycols include, but are not limited to, a polyethylene glycol having an average molecular weight of 1,000 to 40,000 daltons, a polyethylene glycol having an average molecular weight of 2,000 to 20,000 daltons, and a polyethylene glycol having an average molecular weight of 3,000 to 12,000 daltons.

In other embodiments, the IL-2 is covalently conjugated to a polyoxyethylated polyol. Exemplary polyoxyethylated polyols include, but are not limited to, polyoxyethylated sorbitol, polyoxyethylated glucose and polyoxyethylated glycerol. In certain embodiments, the polyoxyethylated polyol is a polyoxyethylated glycerol having an average molecular weight of 1,000 to 40,000.

In any of the methods described herein, multiple cycles of the method of treatment can be administered to the subject for a time period sufficient to effect at least a partial tumor response. In certain embodiments, the time period is at least 6 months. In certain embodiments, the time period is at least 12 months. In certain embodiments, the time period is sufficient to effect a complete tumor response.

In certain embodiments, the method of treatment further comprises multiple cycles of a treatment comprising: a) administering a dose of 9 MIU of IL-2 per day, in 1-3 doses a day, for 3-6 days a week, repeated for 1-24 weeks; and b) administering no IL-2 for 1-4 weeks; administered to said subject for a time period sufficient to effect at least a partial tumor response.

In any of the methods described herein, the IL-2 can be administered by subcutaneous, intraperitoneal, intramuscular, intravenous, oral, pulmonary, nasal, topical, or transdermal administration, or by infusion or suppositories. In a preferred embodiment, the IL-2 is administered subcutaneously.

These and other embodiments of the subject invention will readily occur to those of skill in the art in view of the disclosure herein.

BRIEF DESCRIPTION OF THE FIGURES

FIG. 1 shows a plot of the percentage of subjects exhibiting progression free survival (PFS) versus time in years and a plot of the percentage of surviving subjects versus time in years.

FIG. 5 shows separate plots of the percentage of surviving subjects versus time in years for each of the risk groups. Data for subjects treated with low dose IL-2 are shown with a solid line. Data for subjects treated with chemotherapy are shown with a dashed line.

DETAILED DESCRIPTION OF THE INVENTION

Figure 1:
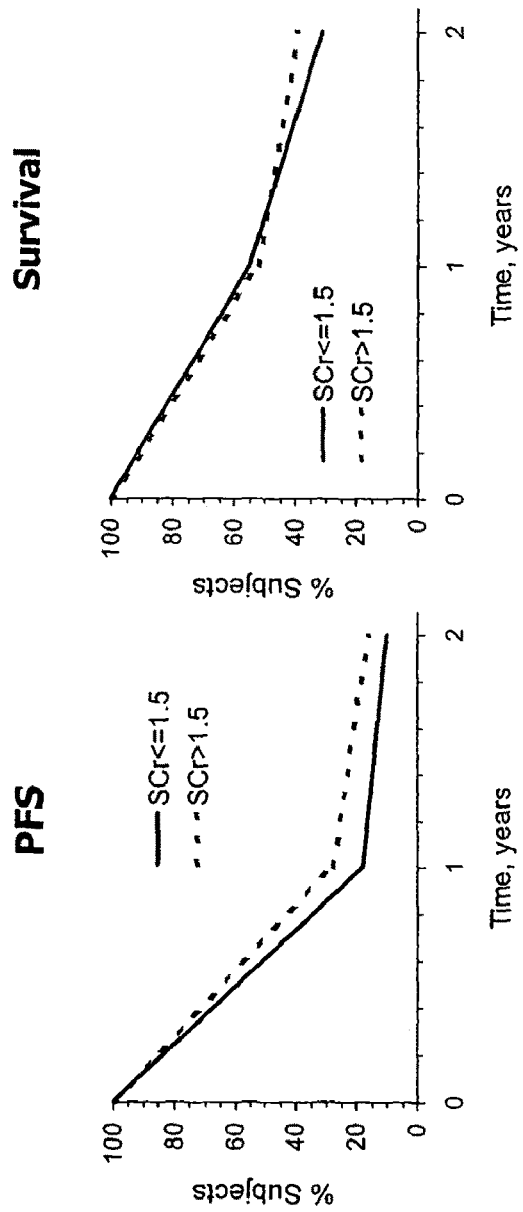
FIG. 1 compares the relative efficacy of low dose IL-2 in patients with metastatic renal cell carcinoma having normal (serum creatinine (SCr)≦1.5 mg/dL) and impaired renal function (SCr>1.5 mg/dL) following the administration regimen described in Example 3.

The practice of the present invention will employ, unless otherwise indicated, conventional methods of pharmacology, chemistry, biochemistry, recombinant DNA techniques and immunology, within the skill of the art. Such techniques are explained fully in the literature. See, e.g., *Handbook of Experimental Immunology*, Vols. I-IV (D. M. Weir and C. C. Blackwell eds., Blackwell Scientific Publications); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein, whether supra or infra, are hereby incorporated by reference in their entireties.

I. Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a chemotherapeutic agent" includes a mixture of two or more such agents, and the like.

The term "IL-2" as used herein is a protein derived from a lymphokine that is produced by normal peripheral blood lymphocytes and is present in the body at low concentrations. IL-2 was first described by Morgan et al. (1976) *Science* 193:1007-1008 and originally called T cell growth factor because of its ability to induce proliferation of stimulated T lymphocytes. It is a protein with a reported molecular weight in the range of 13,000 to 17,000 (Gillis and Watson (1980) *J. Exp. Med.* 159:1709) and has an isoelectric point in the range of 6-8.5. Both full-length IL-2 proteins and biologically active fragments thereof are encompassed by the definition. The term also includes postexpression modifications of the IL-2, for example, glycosylation, acetylation, phosphorylation and the like. Furthermore, for purposes of the present invention, the term "IL-2" refers to a protein which includes modifications, such as deletions, additions and substitutions (generally conservative in nature), to the native sequence, so long as the protein maintains biological activity, i.e., antitumor activity. These modifications may be deliberate, as through site-directed mutagenesis, or may be accidental, such as through mutations of hosts which produce the proteins or errors due to PCR amplification.

The term "derived from" is used herein to identify the original source of a molecule but is not meant to limit the method by which the molecule is made which can be, for example, by chemical synthesis or recombinant means.

The terms "variant," "analog" and "mutein" refer to biologically active derivatives of the reference molecule, that retain desired activity, such as anti-tumor activity in the treatment of renal cell carcinoma described herein. In general, the terms "variant" and "analog" refer to compounds having a native polypeptide sequence and structure with one or more amino acid additions, substitutions (generally conservative in nature) and/or deletions, relative to the native molecule, so long as the modifications do not destroy biological activity and which are "substantially homologous" to the reference molecule as defined below. In general, the amino acid sequences of such analogs will have a high degree of sequence homology to the reference sequence, e.g., amino acid sequence homology of more than 50%, generally more than 60%-70%, even more particularly 80%-85% or more, such as at least 90%-95% or more, when the two sequences are aligned. Often, the analogs will include the same number of amino acids but will include substitutions, as explained herein. The term "mutein" further includes polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and 5,977,301; Nguyen et al., Chem Biol. (2000) 7:463-473; and Simon et al., Proc. Natl. Acad. Sci. USA (1992) 89:9367-9371 for descriptions of peptoids). Preferably, the analog or mutein has at least the same anti-tumor activity as the native molecule. Methods for making polypeptide analogs and muteins are known in the art and are described further below.

As explained above, analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that can tolerate change by reference to Hopp/Woods and Kyte-Doolittle plots, well known in the art.

By "derivative" is intended any suitable modification of the native polypeptide of interest, of a fragment of the native polypeptide, or of their respective analogs, such as glycosylation, phosphorylation, polymer conjugation (such as with polyethylene glycol), or other addition of foreign moieties, so long as the desired biological activity of the native polypeptide is retained. Methods for making polypeptide fragments, analogs, and derivatives are generally available in the art.

By "fragment" is intended a molecule consisting of only a part of the intact full-length sequence and structure. The fragment can include a C-terminal deletion an N-terminal deletion, and/or an internal deletion of the native polypeptide. Active fragments of a particular protein will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, or any integer between 5 amino acids and the full-length sequence, provided that the fragment in question retains biological activity, such as anti-tumor activity, as defined herein.

"Substantially purified" generally refers to isolation of a substance (compound, polynucleotide, protein, polypeptide, polypeptide composition) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

"Homology" refers to the percent identity between two polynucleotide or two polypeptide moieties. Two nucleic acid, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules (the reference sequence and a sequence with unknown % identity to the reference sequence) by aligning the sequences, counting the exact number of matches between the two aligned sequences, dividing by the length of the reference sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning, supra; Nucleic Acid Hybridization*, supra.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

"Renally impaired" as used herein refers to a patient, who has an insufficient glomerular filtration rate. Such a patient is characterized herein by a serum creatinine level (SCr) greater than 1.5 mg/dL.

By "anti-tumor activity" is intended a reduction in the rate of cell proliferation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. Such activity can be assessed using animal models, such as xenograft models of human renal cell carcinoma. See, e.g., Pulkkanen et al., *In Vivo* (2000) 14:393-400 and Everitt et al., *Toxicol. Lett.* (1995) 82-83:621-625 for a description of animal models.

By "therapeutically effective dose or amount" of IL-2 or a variant thereof is intended an amount that, when administered as described herein, brings about a positive therapeutic response, such as anti-tumor activity.

The term "tumor response" as used herein means a reduction or elimination of all measurable lesions. The criteria for tumor response are based on the WHO Reporting Criteria [WHO Offset Publication, 48-World Health Organization, Geneva, Switzerland, (1979)]. Ideally, all uni- or bidimensionally measurable lesions should be measured at each assessment. When multiple lesions are present in any organ, such measurements may not be possible and, under such circumstances, up to 6 representative lesions should be selected, if available.

The term "complete response" (CR) as used herein means a complete disappearance of all clinically detectable malignant disease, determined by 2 assessments at least 4 weeks apart.

The term "partial response" (PR) as used herein means a 50% or greater reduction from baseline in the sum of the products of the longest perpendicular diameters of all measurable disease without progression of evaluable disease and without evidence of any new lesions as determined by at least two consecutive assessments at least four weeks apart. Assessments should show a partial decrease in the size of lytic lesions, recalcifications of lytic lesions, or decreased density of blastic lesions. It is not unusual for IL-2 to cause transient inflammation in sites of metastatic disease. Individual lesions which appear to increase in size do not necessarily disqualify a PR unless the increase is documented on two sequential measurements taken at least 28 days apart.

The term "progressive disease" (PD) as used herein refers to a 25% or greater increase in the size of at least one bidimensionally (product of the largest perpendicular diameters) or unidimensionally measurable lesion; clear worsening of any evaluable lesions; reappearance of any lesions which had disappeared; or the appearance of new lesions; as determined by at least two consecutive assessments at least 28 days apart.

The term "stable disease" (SD) or "no change" as used herein in reference to (a) bidimensionally measurable disease means less than about 50% decrease or less than about 25% increase in the sum of the products of the largest perpendicular diameters of all measurable lesions and (b) unidimensionally measurable disease, means less than about 50% decrease or less than about 25% increase in the sum of the diameters of all lesions. No new lesions should appear. It is the absence of a complete response, partial response, or progression. Because of the slow response of bone lesions to treatment, the designation "no change" should not be applied until at least eight weeks have passed from the start of therapy.

The term "non responder" as used herein means patients with stable disease or minor responses (greater than 25% but less than 50% reduction in tumor burden).

The term "progression" as used herein means a 25% increase in the sum of the products of all measurable lesions over the smallest sum observed, or over baseline if no decrease from baseline; clear worsening of any evaluable lesions; reappearance of any lesions which had disappeared; appearance of any new lesions or sites, including new sites of non-evaluable disease; and/or in cases where an initial tumor flare may occur (hypercalcemia, bone pain, erythema of skin lesions), symptoms must either persist beyond four weeks, or there must be additional evidence of progression.

The term "overall response" as used herein means the response as determined from considering all sites of malignant disease. In subjects with measurable disease, the poorest response shall be the overall response. No change in non-measurable lesions will not detract from a partial response in measurable lesions; i.e., the overall response will be a partial response. No change in non-measurable lesions will reduce a complete response in measurable lesions; i.e., the overall response will be a partial response.

The term "response duration" as used herein means the time from the first documentation of best objective tumor response to the time of progression.

The term "survival" as used herein means the time from the first dose of IL-2 to the time of death.

The term "progression-free survival" (PFS) as used herein means for responders, the time from the first dose of IL-2 to the time of tumor progression, death, or the last clinic visit by patient if still in response.

II. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery of a novel therapeutic methodology for safely and effectively treating renal cell carcinoma by administration of low doses of IL-2. The treatment regimen described herein significantly inhibited tumor growth with lower toxicity and reduced adverse side effects compared to high dose IL-2 treatments.

While the methods of the invention are directed to treatment of an existing tumor, it is recognized that the methods may be useful in preventing further tumor outgrowths arising during therapy. The methods of the invention are particularly useful in the treatment of subjects having metastatic renal cell carcinoma, who have impaired renal function and/or cannot tolerate treatment with high doses of IL-2.

The IL-2 for use in the methods of the invention may be native or obtained by recombinant techniques, and may be from any source, including mammalian sources such as, e.g., mouse, rat, rabbit, primate, pig, and human. IL-2 sequences from a number of species are well known in the art and include but are not limited to, the following: human IL-2 (*Homo sapiens*; precursor sequence, GenBank Accession No. AAH66254; mature sequence represented by residues 21-153 of GenBank Accession No. AAH66254); rhesus monkey IL-2 (*Macaca mulatto*; precursor sequence, GenBank Accession No. P51498; mature sequence represented by residues 21-154 of GenBank Accession No. P51498 sequence); olive baboon IL-2 (*Papio anubis*; precursor sequence, GenBank Accession No. Q865Y1; mature sequence represented by residues 21-154 of GenBank Accession No. Q865Y1 sequence); sooty mangabey IL-2 (*Cercocebus torquatus atys*; precursor sequence, GenBank Accession No. P46649; mature sequence represented by residues 21-154 of GenBank Accession No. P46649 sequence); crab-eating macaque IL-2 (*Macaca fascicularis*; precursor sequence, GenBank Accession No. Q29615; mature sequence represented by residues 21-154 of GenBank Accession No. Q29615 sequence); common gibbon IL-2 (*Hylobates lar*; precursor sequence, GenBank Accession No. ICGI2; mature sequence represented by residues 21-153 of GenBank Accession No. ICGI2 sequence); common squirrel monkey IL-2 (*Saimiri sciureus*; precursor sequence, GenBank Accession No. Q8MKH2; mature sequence represented by residues 21-154 of GenBank Accession No. Q8MKH2 sequence); cow IL-2 (*Bos taurus*; precursor sequence, GenBank Accession No. P05016; mature sequence represented by residues 21-155 of GenBank Accession No. P05016 sequence; see also the variant precursor sequence reported in GenBank Accession No. NP-851340; mature sequence represented by residues 24-158 of GenBank Accession No. NP-851340 sequence); water buffalo IL-2 (*Bubalus bubalis*; precursor sequence, GenBank Q95KP3; mature sequence represented by residues 21-155 of GenBank Q95KP3 sequence); horse IL-2 (*Equus caballus*; precursor sequence, GenBank Accession No. P37997; mature sequence represented by residues 21-149 of GenBank Accession No. P37997 sequence); goat IL-2 (*Capra hircus*; precursor sequence, GenBank Accession No. P36835; mature sequence represented by residues 21-155 of GenBank Accession No. P36835 sequence); sheep IL-2 (*Ovis aries*; precursor sequence, GenBank Accession No. P19114; mature sequence represented by residues 21-155 of GenBank Accession No. P19114 sequence); pig IL-2 (*Sus scrota*; precursor sequence, GenBank Accession No. P26891; mature sequence represented by residues 21-154 of GenBank Accession No. P26891); red deer IL-2 (*Cervus elaphus*; precursor sequence, GenBank Accession No. P51747; mature sequence represented by residues 21-162 of GenBank Accession No. P51747 sequence); dog IL-2 (*Canis familiaris*; precursor sequence, GenBank Accession No. Q29416; mature sequence represented by residues 21-155 of GenBank Accession No. Q29416 sequence); cat IL-2 (*Felis catus*; precursor sequence, GenBank Accession No. Q07885; mature sequence represented by residues 21-154 of GenBank Accession No. Q07885 sequence); rabbit IL-2 (*Oryctolagus cuniculus*; precursor sequence, GenBank Accession No. 077620; mature sequence represented by residues 21-153 of GenBank Accession No. 077620 sequence); killer whale IL-2 (*Orcinus orca*; precursor sequence, GenBank Accession No. 097513; mature sequence represented by residues 21-152 of GenBank Accession No. 097513 sequence); northern elephant seal IL-2 (*Mirounga angustirostris*; precursor sequence, GenBank Accession No. O62641; mature sequence represented by residues 21-154 of GenBank Accession No. O62641 sequence); house mouse IL-2 (*Mus musculus*; precursor sequence, GenBank Accession No. NP_032392; mature sequence represented by residues 21-169 of GenBank Accession No. NP_032392 sequence); western wild mouse IL-2 (*Mus spretus*; precursor sequence, GenBank Accession No. Q08867; mature sequence represented by residues 21-166 of GenBank Accession No. Q08867 sequence); Norway rat IL-2 (*Rattus norvegicus*; precursor sequence, GenBank Accession No. P17108; mature sequence represented by residues 21-155 of GenBank Accession No. P17108); Mongolian gerbil IL-2 (*Meriones unguiculatus*; precursor sequence, GenBank Accession No. Q08081; mature sequence represented by residues 21-155 of GenBank Accession No. Q08081); any of the variant IL-2 polypeptides disclosed in these foregoing GenBank Accession Numbers; each of which GenBank reports are herein incorporated by reference in their entirety. Though any source of IL-2 can be utilized to practice the invention, preferably the IL-2 is derived from a human source, particularly when the subject undergoing therapy is a human. In some embodiments, the IL-2 for use in the methods of the invention is recombinantly produced, for example, recombinant human IL-2 proteins, including, but not limited to, those obtained from microbial hosts.

The compositions useful in the methods of the invention may comprise biologically active variants of IL-2, including variants of IL-2 from any species. Such variants should retain the desired biological activity of the native polypeptide such that the pharmaceutical composition comprising the variant polypeptide has the same therapeutic effect as the pharmaceutical composition comprising the native polypeptide when administered to a subject. That is, the variant polypeptide will serve as a therapeutically active component in the pharmaceutical composition in a manner similar to that observed for the native polypeptide. Methods are available in the art for determining whether a variant polypeptide retains the desired biological activity, and hence serves as a therapeutically active component in the pharmaceutical composition. Biological activity can be measured using assays specifically designed for measuring activity of the native polypeptide or protein, including assays described in the present invention. Additionally, antibodies raised against a biologically active native polypeptide can be tested for their ability to bind to the variant polypeptide, where effective binding is indicative of a polypeptide having a conformation similar to that of the native polypeptide.

Suitable biologically active variants of native or naturally occurring IL-2 can be fragments, analogs, and derivatives of that polypeptide, as defined above.

For example, amino acid sequence variants of the polypeptide can be prepared by mutations in the cloned DNA sequence encoding the native polypeptide of interest. Methods for mutagenesis and nucleotide sequence alterations are well known in the art. See, for example, Walker and Gaastra, eds. (1983) Techniques in Molecular Biology (MacMillan Publishing Company, New York); Kunkel (1985) *Proc. Natl. Acad. Sci. USA* 82:488-492; Kunkel et al. (1987) *Methods Enzymol.* 154:367-382; Sambrook et al. (1989) Molecular Cloning: A Laboratory Manual (Cold Spring Harbor Laboratory Press, Plainview, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in Atlas of Protein Sequence and Structure (Natl. Biomed. Res. Found., Washington, D.C.), herein incorporated by reference. Conservative substitutions, such as exchanging one amino acid with another having similar properties, may be preferred. Examples of conservative substitutions include, but are not limited to, Gly⇔Ala, Val⇔Ile⇔Leu, Asp⇔Glu, Lys⇔Arg, Asn⇔Gln, and Phe⇔Trp⇔Tyr.

Guidance as to regions of the IL-2 protein that can be altered either via residue substitutions, deletions, or insertions can be found in the art. See, for example, the structure/function relationships and/or binding studies discussed in Bazan (1992) *Science* 257:410-412; McKay (1992) *Science* 257:412; Theze et al. (1996) *Immunol. Today* 17:481-486; Buchli and Ciardelli (1993) *Arch. Biochem. Biophys.* 307: 411-415; Collins et al. (1988) *Proc. Natl. Acad. Sci. USA* 85:7709-7713; Kuziel et al. (1993) *J. Immunol.* 150:5731; Eckenberg et al. (1997) *Cytokine* 9:488-498; the contents of which are herein incorporated by reference in their entirety.

In constructing variants of the IL-2 polypeptide of interest, modifications are made such that variants continue to possess the desired activity. Obviously, any mutations made in the DNA encoding the variant polypeptide must not place the sequence out of reading frame and preferably will not create complementary regions that could produce secondary mRNA structure. See EP Patent Application Publication No. 75,444.

Biologically active variants of IL-2 will generally have at least about 70%, preferably at least about 80%, more preferably at least about 90% to 95% or more, and most preferably at least about 98%, 99% or more amino acid sequence identity to the amino acid sequence of the reference IL-2 polypeptide molecule, such as native human IL-2, which serves as the basis for comparison. Percent sequence identity is determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman, *Adv. Appl. Math.* (1981) 2:482-489. A variant may, for example, differ by as few as 1 to 15 amino acid residues, as few as 1 to 10 residues, such as 6-10, as few as 5, as few as 4, 3, 2, or even 1 amino acid residue.

With respect to optimal alignment of two amino acid sequences, the contiguous segment of the variant amino acid sequence may have the same number of amino acids, additional amino acid residues or deleted amino acid residues with respect to the reference amino acid sequence. The contiguous segment used for comparison to the reference amino acid sequence will include at least 20 contiguous amino acid residues, and may be 30, 40, 50, or more amino acid residues. Corrections for sequence identity associated with conservative residue substitutions or gaps can be made (see Smith-Waterman homology search algorithm). A biologically active variant of a native IL-2 polypeptide of interest may differ from the native polypeptide by as few as 1-15 amino acids, as few as 1-10, such as 6-10, as few as 5, as few as 4, 3, 2, or even 1 amino acid residue.

The precise chemical structure of a polypeptide having IL-2 activity depends on a number of factors. As ionizable amino and carboxyl groups are present in the molecule, a particular polypeptide may be obtained as an acidic or basic salt, or in neutral form. All such preparations that retain their biological activity when placed in suitable environmental conditions are included in the definition of polypeptides having IL-2 activity as used herein. Further, the primary amino acid sequence of the polypeptide may be augmented by derivatization using sugar moieties (glycosylation) or by other supplementary molecules such as lipids, phosphate, acetyl groups and the like. It may also be augmented by conjugation with saccharides. Certain aspects of such augmentation are accomplished through post-translational processing systems of the producing host; other such modifications may be introduced in vitro. In any event, such modifications are included in the definition of an IL-2 polypeptide used herein so long as the IL-2 activity of the polypeptide is not destroyed. It is expected that such modifications may quantitatively or qualitatively affect the activity, either by enhancing or diminishing the activity of the polypeptide, in the various assays. Further, individual amino acid residues in the chain may be modified by oxidation, reduction, or other derivatization, and the polypeptide may be cleaved to obtain fragments that retain activity. Such alterations that do not destroy activity do not remove the polypeptide sequence from the definition of IL-2 polypeptides of interest as used herein.

The art provides substantial guidance regarding the preparation and use of polypeptide variants. In preparing the IL-2 variants, one of skill in the art can readily determine which modifications to the native protein nucleotide or amino acid sequence will result in a variant that is suitable for use as a therapeutically active component of a pharmaceutical composition used in the methods of the present invention.

The IL-2 or variants thereof for use in the methods of the present invention may be from any source, but preferably is recombinantly produced. By "recombinant IL-2" or "recombinant IL-2 variant" is intended interleukin-2 or variant thereof that has comparable biological activity to native-sequence IL-2 and that has been prepared by recombinant DNA techniques as described, for example, by Taniguchi et al. (1983) *Nature* 302:305-310 and Devos (1983) *Nucleic Acids*

Research 11:4307-4323 or mutationally altered IL-2 as described by Wang et al. (1984) Science 224:1431-1433. In general, the gene coding for IL-2 is cloned and then expressed in transformed organisms, preferably a microorganism, and most preferably E. coli, as described herein. The host organism expresses the foreign gene to produce IL-2 under expression conditions. Synthetic recombinant IL-2 can also be made in eukaryotes, such as yeast or human cells. Processes for growing, harvesting, disrupting, or extracting the IL-2 from cells are substantially described in, for example, U.S. Pat. Nos. 4,604,377; 4,738,927; 4,656,132; 4,569,790; 4,748,234; 4,530,787; 4,572,798; 4,748,234; and 4,931,543, herein incorporated by reference in their entireties.

For examples of variant IL-2 proteins, see European Patent (EP) Publication No. EP 136,489 (which discloses one or more of the following alterations in the amino acid sequence of naturally occurring IL-2: Asn26 to Gln26; Trp121 to Phe121; Cys58 to Ser58 or Ala58, Cys105 to Ser105 or Ala105; Cys125 to Ser125 or Ala125; deletion of all residues following Arg 120; and the Met-1 forms thereof); and the recombinant IL-2 muteins described in European Patent Application No. 83306221.9, filed Oct. 13, 1983 (published May 30, 1984 under Publication No. EP 109,748), which is the equivalent to Belgian Patent No. 893,016, and commonly owned U.S. Pat. No. 4,518,584 (which disclose recombinant human IL-2 mutein wherein the cysteine at position 125, numbered in accordance with native human IL-2, is deleted or replaced by a neutral amino acid; alanyl-ser125-IL-2; and des-alanyl-ser125-IL-2). See also U.S. Pat. No. 4,752,585 (which discloses the following variant IL-2 proteins: ala104 ser125 IL-2, ala104 IL-2, ala104 ala125 IL-2, val104 ser125 IL-2, val104 IL-2, val104 ala125 IL-2, des-ala1 ala104 ser125 IL-2, des-ala1 ala104 IL-2, des-ala1 ala104 ala125 IL-2, des-ala1 val104 ser125 IL-2, des-ala1 val104 IL-2, des-ala1 val104 ala125 IL-2, des-ala1 des-pro2 ala104 ser125 IL-2, des-ala1 des-pro2 ala104 IL-2, des-ala1 des-pro2 ala104 ala125 IL-2, des-ala1 des-pro2 val104 ser125 IL-2, des-ala1 des-pro2 val104 IL-2, des-ala1 des-pro2 val104 ala125 IL-2, des-ala1 des-pro2 des-thr3 ala104 ser125 IL-2, des-ala1 des-pro2 des-thr3 ala104 IL-2, des-ala1 des-pro2 des-thr3 ala104 ala125 IL-2, des-ala1 des-pro2 des-thr3 val104 ser125 IL-2, des-ala1 des-pro2 des-thr3 val104 IL-2, des-ala1 des-pro2 des-thr3 val104 ala125 IL-2, des-ala1 des-pro2 des-thr3 des-ser4 ala104 ser125 IL-2, des-ala1 des-pro2 des-thr3 des-ser4 ala104 IL-2, des-ala1 des-pro2 des-thr3 des-ser4 ala104 ala125 IL-2, des-ala1 des-pro2 des-thr3 des-ser4 val104 ser125 IL-2, des-ala1 des-pro2 des-thr3 des-ser4 val104 IL-2, des-ala1 des-pro2 des-thr3 des-ser4 val104 ala125 IL-2, des-ala1 des-pro2 des-thr3 des-ser4 des-ser5 ala104 ser125 IL-2, des-ala1 des-pro2 des-thr3 des-ser4 des-ser5 ala104 IL-2, des-ala1 des-pro2 des-thr3 des-ser4 des-ser5 ala104 ala125 IL-2, des-ala1 des-pro2 des-thr3 des-ser4 des-ser5 val104 ser125 IL-2, des-ala1 des-pro2 des-thr3 des-ser4 des-ser5 val104 IL-2, des-ala1 des-pro2 des-thr3 des-ser4 des-ser5 val104 ala125 IL-2, des-ala1 des-pro2 des-thr3 des-ser4 des-ser5 des-ser6 ala104 ala125 IL-2, des-ala1 des-pro2 des-thr3 des-ser4 des-ser5 des-ser6 ala104 IL-2, des-ala1 des-pro2 des-thr3 des-ser4 des-ser5 des-ser6 ala104 ser125 IL-2, des-ala1 des-pro2 des-thr3 des-ser4 des-ser5 des-ser6 val104 ser125 IL-2, des-ala1 des-pro2 des-thr3 des-ser4 des-ser5 des-ser6 val104 IL-2, and des-ala1 des-pro2 des-thr3 des-ser4 des-ser5 des-ser6 val104 ala125 IL-2) and U.S. Pat. No. 4,931,543 (which discloses the IL-2 mutein des-alanyl-1, serine-125 human IL-2 used in the examples herein, as well as the other IL-2 muteins).

Also see European Patent Publication No. EP 200,280 (published Dec. 10, 1986), which discloses recombinant IL-2 muteins wherein the methionine at position 104 has been replaced by a conservative amino acid. Examples include the following muteins: ser4 des-ser5 ala104 IL-2; des-ala1 des-pro2 des-thr3 des-ser4 des-ser5 ala104 ala125 IL-2; des-ala1 des-pro2 des-thr3 des-ser4 des-ser5 glu104 ser125 IL-2; des-ala1 des-pro2 des-thr3 des-ser4 des-ser5 glu104 IL-2; des-ala1 des-pro2 des-thr3 des-ser4 des-ser5 glu104 ala125 IL-2; des-ala1 des-pro2 des-thr3 des-ser4 des-ser5 des-ser6 ala104 ala125 IL-2; des-ala1 des-pro2 des-thr3 des-ser4 des-ser5 des-ser6 ala104 IL-2; des-ala1 des-pro2 des-thr3 des-ser4 des-ser5 des-ser6 ala104 ser125 IL-2; des-ala1 des-pro2 des-thr3 des-ser4 des-ser5 des-ser6 glu104 ser125 IL-2; des-ala1 des-pro2 des-thr3 des-ser4 des-ser5 des-ser6 glu104 IL-2; and des-ala1 des-pro2 des-thr3 des-ser4 des-ser5 des-ser6 glu104 ala125 IL-2. See also European Patent Publication No. EP 118,617 and U.S. Pat. No. 5,700,913, which disclose unglycosylated human IL-2 variants bearing alanine instead of methionine as the N-terminal amino acid as found in the native molecule; an unglycosylated human IL-2 with the initial methionine deleted such that proline is the N-terminal amino acid; and an unglycosylated human IL-2 with an alanine inserted between the N-terminal methionine and proline amino acids.

Other IL-2 muteins include those disclosed in WO 99/60128 (substitutions of the aspartate at position 20 with histidine or isoleucine, the asparagine at position 88 with arginine, glycine, or isoleucine, or the glutamine at position126 with leucine or gulatamic acid), which reportedly have selective activity for high affinity IL-2 receptors expressed by cells expressing T cell receptors in preference to NK cells and reduced IL-2 toxicity; the muteins disclosed in U.S. Pat. No. 5,229,109 (substitutions of arginine at position 38 with alanine, or substitutions of phenylalanine at position 42 with lysine), which exhibit reduced binding to the high affinity IL-2 receptor when compared to native IL-2 while maintaining the ability to stimulate LAK cells; the muteins disclosed in International Publication No. WO 00/58456 (altering or deleting a naturally occurring (x)D(y) sequence in native IL-2 where D is aspartic acid, (x) is leucine, isoleucine, glycine, or valine, and (y) is valine, leucine or serine), which are claimed to reduce vascular leak syndrome; the IL-2 p1-30 peptide disclosed in International Publication No. WO 00/04048 (corresponding to the first 30 amino acids of IL-2, which contains the entire a-helix A of IL-2 and interacts with the b chain of the IL-2 receptor), which reportedly stimulates NK cells and induction of LAK cells; and a mutant form of the IL-2 p1-30 peptide also disclosed in WO 00/04048 (substitution of aspartic acid at position 20 with lysine), which reportedly is unable to induce vascular bleeds but remains capable of generating LAK cells. Additionally, IL-2 can be modified with polyethylene glycol to provide enhanced solubility and an altered pharmokinetic profile (see U.S. Pat. No. 4,766, 106).

Additional examples of IL-2 muteins with predicted reduced toxicity are disclosed in U.S. Provisional Application Ser. No. 60/550,868, filed Mar. 5, 2004, herein incorporated by reference in its entirety. These muteins comprise the amino acid sequence of mature human IL-2 with a serine substituted for cysteine at position 125 of the mature human IL-2 sequence and at least one additional amino acid substitution within the mature human IL-2 sequence such that the mutein has the following functional characteristics: 1) maintains or enhances proliferation of natural killer (NK) cells, and 2) induces a decreased level of pro-inflammatory cytokine production by NK cells; as compared with a similar amount of des-alanyl-1, C125S human IL-2 or C125S human IL-2 under comparable assay conditions. In some embodiments, the additional substitution is selected from the group consisting of T7A, T7D, T7R, K8L, K9A, K9D, K9R, K9S, K9V, K9W, T10K, T10N, Q11A, Q11R, Q11T, E15A, H16D, H16E, L19D, L19E, D20E, I24L, K32A, K32W, N33E, P34E, P34R, P34S, P34T, P34V, K35D, K35I, K35L, K35M, K35N, K35P, K35Q, K35T, L36A, L36D, L36E, L36F, L36G, L36H, L36I, L36K, L36M, L36N, L36P, L36R, L36S, L36W, L36Y, R38D, R38G, R38N, R38P, R38S, L40D, L40G, L40N, L40S, T41E, T41G, F42A, F42E, F42R, F42T, F42V, K43H, F44K, M46I, E61K, E61M, E61R, E62T, E62Y, K64D, K64E, K64G, K64L, K64Q, K64R, P65D, P65E, P65F, P65G, P65H, P65I, P65K, P65L, P65N, P65Q, P65R, P65S, P65T, P65V, P65W, P65Y, L66A, L66F, E67A, L72G, L72N, L72T, F78S, F78W, H79F, H79M, H79N, H79P, H79Q, H79S, H79V, L80E, L80F, L80G, L80K, L80N, L80R, L80T, L80V, L80W, L80Y, R81E, R81K, R81L, R81M, R81N, R81P, R81T, D84R, S87T, N88D, N88H, N88T, V91A, V91D, V91E, V91F, V91G, V91N, V91Q, V91W, L94A, L94I, L94T, L94V, L94Y, E95D, E95G, E95M, T102S, T102V, M104G, E106K, Y107H, Y107K, Y107L, Y107Q, Y107R, Y107T, E116G, N119Q, T123S, T123C, Q126I, and Q126V; where the amino acid residue position is relative to numbering of the mature human IL-2 amino acid sequence. In other embodiments, these muteins comprise the amino acid sequence of mature human IL-2 with an alanine substituted for cysteine at position 125 of the mature human IL-2 sequence and at least one additional amino acid substitution within the mature human IL-2 sequence such that the mutein has these same functional characteristics. In some embodiments, the additional substitution is selected from the group consisting of T7A, T7D, T7R, K8L, K9A, K9D, K9R, K9S, K9V, K9W, T10K, T10N, Q11A, Q11R, Q11T, E15A, H16D, H16E, L19D, L19E, D20E, I24L, K32A, K32W, N33E, P34E, P34R, P34S, P34T, P34V, K35D, K35I, K35L, K35M, K35N, K35P, K35Q, K35T, L36A, L36D, L36E, L36F, L36G, L36H, L36I, L36K, L36M, L36N, L36P, L36R, L36S, L36W, L36Y, R38D, R38G, R38N, R38P, R38S, L40D, L40G, L40N, L40S, T41E, T41G, F42A, F42E, F42R, F42T, F42V, K43H, F44K, M46I, E61K, E61M, E61R, E62T, E62Y, K64D, K64E, K64G, K64L, K64Q, K64R, P65D, P65E, P65F, P65G, P65H, P65I, P65K, P65L, P65N, P65Q, P65R, P65S, P65T, P65V, P65W, P65Y, L66A, L66F, E67A, L72G, L72N, L72T, F78S, F78W, H79F, H79M, H79N, H79Q, H79S, H79V, L80E, L80F, L80G, L80K, L80N, L80R, L80T, L80V, L80W, L80Y, R81E, R81K, R81L, R81M, R81N, R81P, R81T, D84R, S87T, N88D, N88H, N88T, V91A, V91D, V91E, V91F, V91G, V91N, V91Q, V91W, L94A, L94I, L94T, L94V, L94Y, E95D, E95G, E95M, T102S, T102V, M104G, E106K, Y107H, Y107K, Y107L, Y107Q, Y107R, Y107T, E116G, N119Q, T123S, T123C, Q126I, and Q126V; where the amino acid residue position is relative to numbering of the mature human IL-2 amino acid sequence. In alternative embodiments, these muteins comprise the amino acid sequence of mature human IL-2 with at least one additional amino acid substitution within the mature human IL-2 sequence such that the mutein has these same functional characteristics. In some embodiments, the additional substitution is selected from the group consisting of T7A, T7D, T7R, K8L, K9A, K9D, K9R, K9S, K9V, K9W, T10K, T10N, Q11A, Q11R, Q11T, E15A, H16D, H16E, L19D, L19E, D20E, I24L, K32A, K32W, N33E, P34E, P34R, P34S, P34T, P34V, K35D, K35I, K35L, K35M, K35N, K35P, K35Q, K35T, L36A, L36D, L36E, L36F, L36G, L36H, L36I, L36K, L36M, L36N, L36P, L36R, L36S, L36W, L36Y, R38D, R38G, R38N, R38P, R38S, L40D, L40G, L40N, L40S, T41E, T41G, F42A, F42E, F42R, F42T, F42V, K43H, F44K, M46I, E61K, E61M, E61R, E62T, E62Y, K64D, K64E, K64G, K64L, K64Q, K64R, P65D, P65E, P65F, P65G, P65H, P65I, P65K, P65L, P65N, P65Q, P65R, P65S, P65T, P65V, P65W, P65Y, L66A, L66F, E67A, L72G, L72N, L72T, F78S, F78W, H79F, H79M, H79N, H79P, H79Q, H79S, H79V, L80E, L80F, L80G, L80K, L80N, L80R, L80T, L80V, L80W, L80Y, R81E, R81K, R81L, R81M, R81N, R81P, R81T, D84R, S87T, N88D, N88H, N88T, V91A, V91D, V91E, V91F, V91G, V91N, V91Q, V91W, L94A, L94I, L94T, L94V, L94Y, E95D, E95G, E95M, T102S, T102V, M104G, E106K, Y107H, Y107K, Y107L, Y107Q, Y107R, Y107T, E116G, N119Q, T123S, T123C, Q126I, and Q126V; where the amino acid residue position is relative to numbering of the mature human IL-2 amino acid sequence. Additional muteins disclosed in U.S. Provisional Application Ser. No. 60/550,868 include the foregoing identified muteins, with the exception of having the initial alanine residue at position 1 of the mature human IL-2 sequence deleted.

The term IL-2 as used herein is also intended to include IL-2 fusions or conjugates comprising IL-2 fused to a second protein or covalently conjugated to polyproline or a water-soluble polymer to reduce dosing frequencies or to improve IL-2 tolerability. For example, the IL-2 (or a variant thereof as defined herein) can be fused to human albumin or an albumin fragment using methods known in the art (see WO 01/79258). Alternatively, the IL-2 can be covalently conjugated to polyproline or polyethylene glycol homopolymers and polyoxyethylated polyols, wherein the homopolymer is unsubstituted or substituted at one end with an alkyl group and the polyol is unsubstituted, using methods known in the art (see, for example, U.S. Pat. Nos. 4,766,106, 5,206,344, 4,894,226, and 5,830,452).

Any pharmaceutical composition comprising IL-2 as the therapeutically active component can be used in the methods of the invention. Such pharmaceutical compositions are known in the art and include, but are not limited to, those disclosed in U.S. Pat. Nos. 4,745,180; 4,766,106; 4,816,440; 4,894,226; 4,931,544; and 5,078,997; herein incorporated by reference. Thus liquid, lyophilized, or spray-dried compositions comprising IL-2 or variants thereof that are known in the art may be prepared as an aqueous or nonaqueous solution or suspension for subsequent administration to a subject in accordance with the methods of the invention. Each of these compositions will comprise IL-2 or variants thereof as a therapeutically or prophylactically active component. By "therapeutically or prophylactically active component" is intended the IL-2 or variants thereof is specifically incorporated into the composition to bring about a desired therapeutic or prophylactic response with regard to treatment or prevention of a disease or condition within a subject when the pharmaceutical composition is administered to that subject. Preferably the pharmaceutical compositions comprise appropriate stabilizing agents, bulking agents, or both to minimize problems associated with loss of protein stability and biological activity during preparation and storage.

In preferred embodiments of the invention, the IL-2 containing pharmaceutical compositions useful in the methods of the invention are compositions comprising stabilized monomeric IL-2 or variants thereof, compositions comprising multimeric IL-2 or variants thereof, and compositions comprising stabilized lyophilized or spray-dried IL-2 or variants thereof.

Pharmaceutical compositions comprising stabilized monomeric IL-2 or variants thereof are disclosed in PCT application No. PCT/US00/27156, filed Oct. 3, 2000, the disclosure of which is herein incorporated by reference. By "monomeric" IL-2 is intended the protein molecules are present substantially in their monomer form, not in an aggregated form, in the pharmaceutical compositions described herein. Hence covalent or hydrophobic oligomers or aggregates of IL-2 are not present. Briefly, the IL-2 or variants thereof in these liquid compositions is formulated with an amount of an amino acid base sufficient to decrease aggregate formation of IL-2 or variants thereof during storage. The amino acid base is an amino acid or a combination of amino acids, where any given amino acid is present either in its free base form or in its salt form. Preferred amino acids are selected from the group consisting of arginine, lysine, aspartic acid, and glutamic acid. These compositions further comprise a buffering agent to maintain pH of the liquid compositions within an acceptable range for stability of IL-2 or variants thereof, where the buffering agent is an acid substantially free of its salt form, an acid in its salt form, or a mixture of an acid and its salt form. Preferably the acid is selected from the group consisting of succinic acid, citric acid, phosphoric acid, and glutamic acid. Such compositions are referred to herein as stabilized monomeric IL-2 pharmaceutical compositions.

The amino acid base in these compositions serves to stabilize the IL-2 or variants thereof against aggregate formation during storage of the liquid pharmaceutical composition, while use of an acid substantially free of its salt form, an acid in its salt form, or a mixture of an acid and its salt form as the buffering agent results in a liquid composition having an osmolarity that is nearly isotonic. The liquid pharmaceutical composition may additionally incorporate other stabilizing agents, more particularly methionine, a nonionic surfactant such as polysorbate 80, and EDTA, to further increase stability of the polypeptide. Such liquid pharmaceutical compositions are said to be stabilized, as addition of amino acid base in combination with an acid substantially free of its salt form, an acid in its salt form, or a mixture of an acid and its salt form, results in the compositions having increased storage stability relative to liquid pharmaceutical compositions formulated in the absence of the combination of these two components.

These liquid pharmaceutical compositions comprising stabilized monomeric IL-2 or variants thereof may either be used in an aqueous liquid form, or stored for later use in a frozen state, or in a dried form for later reconstitution into a liquid form or other form suitable for administration to a subject in accordance with the methods of present invention. By "dried form" is intended the liquid pharmaceutical composition or formulation is dried either by freeze drying (i.e., lyophilization; see, for example, Williams and Polli (1984) *J. Parenteral Sci. Technol.* 38:48-59), spray drying (see Masters (1991) in *Spray-Drying Handbook* (5th ed; Longman Scientific and Technical, Essez, U.K.), pp. 491-676; Broadhead et al. (1992) *Drug Devel. Ind. Pharm.* 18:1169-1206; and Mumenthaler et al. (1994) *Pharm. Res.* 11:12-20), or air drying (Carpenter and Crowe (1988) *Cryobiology* 25:459-470; and Roser (1991) *Biopharm.* 4:47-53).

Other examples of IL-2 formulations that comprise IL-2 in its nonaggregated monomeric state include those described in Whittington and Faulds (1993) *Drugs* 46(3):446-514. These formulations include the recombinant IL-2 product in which the recombinant IL-2 mutein Teceleukin (unglycosylated human IL-2 with a methionine residue added at the amino-terminal) is formulated with 0.25% human serum albumin in a lyophilized powder that is reconstituted in isotonic saline, and the recombinant IL-2 mutein Bioleukin (human IL-2 with a methionine residue added at the amino-terminal, and a substitution of the cysteine residue at position 125 of the human IL-2 sequence with alanine) formulated such that 0.1 to 1.0 mg/ml IL-2 mutein is combined with acid, wherein the formulation has a pH of 3.0 to 4.0, advantageously no buffer, and a conductivity of less than 1000 mmhos/cm (advantageously less than 500 mmhos/cm). See EP 373,679; Xhang et al. (1996) *Pharmaceut. Res.* 13(4):643-644; and Prestrelski et al. (1995) *Pharmaceut. Res.* 12(9):1250-1258.

Examples of pharmaceutical compositions comprising multimeric IL-2 or variants thereof are disclosed in commonly owned U.S. Pat. No. 4,604,377, the disclosure of which is herein incorporated by reference. By "multimeric" is intended the protein molecules are present in the pharmaceutical composition in a microaggregated form having an average molecular association of 10-50 molecules. These multimers are present as loosely bound, physically-associated IL-2 molecules. A lyophilized form of these compositions is available commercially under the tradename Proleukin® (Chiron Corporation, Emeryville, Calif.). The lyophilized formulations disclosed in this reference comprise selectively oxidized, microbially produced recombinant IL-2 in which the recombinant IL-2 is admixed with a water soluble carrier such as mannitol that provides bulk, and a sufficient amount of sodium dodecyl sulfate to ensure the solubility of the recombinant IL-2 in water. These compositions are suitable for reconstitution in aqueous injections for parenteral administration and are stable and well tolerated in human patients. When reconstituted, the IL-2 or variants thereof retains its multimeric state. Such lyophilized or liquid compositions comprising multimeric IL-2 or variants thereof are encompassed by the methods of the present invention. Such compositions are referred to herein as multimeric IL-2 pharmaceutical compositions.

The methods of the present invention may also use stabilized lyophilized or spray-dried pharmaceutical compositions comprising IL-2 or variants thereof, which may be reconstituted into a liquid or other suitable form for administration in accordance with methods of the invention. Such pharmaceutical compositions are disclosed in copending application U.S. Ser. No. 09/724,810, filed Nov. 28, 2000 and International Application PCT/US00/35452, filed Dec. 27, 2000, herein incorporated by reference in their entireties. These compositions may further comprise at least one bulking agent, at least one agent in an amount sufficient to stabilize the protein during the drying process, or both. By "stabilized" is intended the IL-2 protein or variants thereof retains its monomeric or multimeric form as well as its other key properties of quality, purity, and potency following lyophilization or spray-drying to obtain the solid or dry powder form of the composition. In these compositions, preferred carrier materials for use as a bulking agent include glycine, mannitol, alanine, valine, or any combination thereof, most preferably glycine. The bulking agent is present in the formulation in the range of 0% to about 10% (w/v), depending upon the agent used. Preferred carrier materials for use as a stabilizing agent include any sugar or sugar alcohol or any amino acid. Preferred sugars include sucrose, trehalose, raffinose, stachyose, sorbitol, glucose, lactose, dextrose or any combination thereof, preferably sucrose. When the stabilizing agent is a sugar, it is present in the range of about 0% to about 9.0% (w/v), preferably about 0.5% to about 5.0%, more preferably about 1.0% to about 3.0%, most preferably about 1.0%. When the stabilizing agent is an amino acid, it is present in the range of about 0% to about 1.0% (w/v), preferably about 0.3% to about 0.7%, most preferably about 0.5%. These stabilized lyophilized or spray-dried compositions may optionally comprise methionine, ethylenediaminetetracetic acid (EDTA) or one of its salts such as disodium EDTA or other chelating agent, which protect the IL-2 or variants thereof against methionine oxidation. Use of these agents in this manner is described in copending U.S. Provisional Application Ser. No.

60/157696, herein incorporated by reference. The stabilized lyophilized or spray-dried compositions may be formulated using a buffering agent, which maintains the pH of the pharmaceutical composition within an acceptable range, preferably between about pH 4.0 to about pH 8.5, when in a liquid phase, such as during the formulation process or following reconstitution of the dried form of the composition. Buffers are chosen such that they are compatible with the drying process and do not affect the quality, purity, potency, and stability of the protein during processing and upon storage.

The previously described stabilized monomeric, multimeric, and stabilized lyophilized or spray-dried IL-2 pharmaceutical compositions represent suitable compositions for use in the methods of the invention. However, any pharmaceutical composition comprising IL-2 or variant thereof as a therapeutically active component is encompassed by the methods of the invention.

Administration

At least one therapeutically effective cycle of treatment with low doses of IL-2 or a variant thereof, will be administered. By "therapeutically effective cycle of treatment" is intended a cycle of treatment that when administered, brings about a positive therapeutic response with respect to treatment of an individual for renal cell carcinoma, particularly metastatic renal cell carcinoma. Of particular interest is a cycle of treatment with low doses of IL-2 that provides an anti-tumor effect, as defined herein. By "positive therapeutic response" is intended the individual undergoing the treatment according to the invention exhibits an improvement in one or more symptoms of renal cell carcinoma for which the individual is undergoing therapy.

Thus, for example, a "positive therapeutic response" would be an improvement in the disease in association with the therapy, and/or an improvement in one or more symptoms of the disease in association with the therapy. Therefore, for example, a positive therapeutic response would refer to one or more of the following improvements in the disease: (1) reduction in tumor size; (2) reduction in the number of cancer cells; (3) inhibition (i.e., slowing to some extent, preferably halting) of tumor growth; (4) inhibition (i.e., slowing to some extent, preferably halting) of cancer cell infiltration into peripheral organs; (5) inhibition (i.e., slowing to some extent, preferably halting) of tumor metastasis; and (6) some extent of relief from one or more symptoms associated with the cancer. Such therapeutic responses may be further characterized as to degree of improvement. Thus, for example, an improvement may be characterized as a complete response. By "complete response" is intended documentation of the disappearance of all symptoms and signs of all measurable or evaluable disease confirmed by physical examination, laboratory, nuclear and radiographic studies (i.e., CT (computer tomography) and/or MRI (magnetic resonance imaging)), and other non-invasive procedures repeated for all initial abnormalities or sites positive at the time of entry into the study. Alternatively, an improvement in the disease may be categorized as being a partial response. By "partial response" is intended a reduction of greater than 50% in the sum of the products of the perpendicular diameters of all measurable lesions when compared with pretreatment measurements, and no progression of evaluable disease, nor formation of any new lesions for at least 28 days.

In certain embodiments of the invention, the pharmaceutical composition comprising IL-2 or a variant thereof, is a sustained-release formulation, or a formulation that is administered using a sustained-release device. Such devices are well known in the art, and include, for example, transdermal patches; and miniature implantable pumps that can provide for drug delivery over time in a continuous, steady-state fashion at a variety of doses to achieve a sustained-release effect with a non-sustained-release pharmaceutical composition.

Pharmaceutical compositions comprising IL-2 or a variant thereof may be administered in accordance with any medically acceptable method known in the art. Suitable routes of administration include parenteral administration, such as subcutaneous (SC), intraperitoneal (IP), intramuscular (IM), intravenous (IV), or infusion, oral and pulmonary, nasal, topical, transdermal, and suppositories. Where the composition is administered via pulmonary delivery, the therapeutically effective dose is adjusted such that the soluble level of the agent, such as the IL-2 or variant thereof in the bloodstream, is equivalent to that obtained with a therapeutically effective dose that is administered parenterally, for example SC, IP, IM, or IV. In some embodiments of the invention, the pharmaceutical composition comprising IL-2 or a variant thereof is administered by IM or SC injection, particularly by IM or SC injection locally to the region where the therapeutic agent or agents used in the cancer therapy protocol are administered.

Factors influencing the amount of IL-2 to be administered include, but are not limited to, the mode of administration, the frequency of administration, the particular disease undergoing therapy, the severity of the disease, the history of the disease, whether the individual is undergoing concurrent therapy with another therapeutic agent, and the age, height, weight, health, and physical condition of the individual undergoing therapy. Generally, a higher dosage of this agent is preferred with increasing weight of the subject undergoing therapy.

In order to achieve efficacy, the IL-2 blood level must be above a specific level for a specific time. Efficacy is dose dependent and higher levels of IL-2 contribute to greater anti-tumor effects. In order to minimize toxicity, the IL-2 blood level must be below a certain level within a specific time and for a specific time (there must be a "rest period" to allow clearance of IL-2). That is, the drug must be below a certain level by a certain time before the next dose is given. Shorter rests between doses contribute to. greater toxicity.

In certain embodiments, the method of treatment of a patient having renal cell carcinoma comprises a treatment cycle with low dose IL-2 (1-52 MIU) followed by a rest period to allow the patient to "recover" from the undesirable effects of IL-2. Multiple doses of IL-2 or a variant thereof can be administered according to a daily dosing regimen, for example, 1-52 MIU of IL-2, or more preferably 9-18 MIU of IL-2, is administered per day in one to three doses per day, for three to six days a week, for 1-24 weeks, followed by a rest period. Preferably, the rest period is one to four weeks between dosing regimens. Thereafter, a new schedule of IL-2 dosing may be administered to provide the immune system with another boost. In certain embodiments, the second cycle of treatment comprises administering 9 MIU in one to three doses per day, for three to six days a week, for 1-24 weeks, followed by a rest period.

In certain embodiments, the method of treatment of a patient having renal cell carcinoma comprises a treatment cycle that consists of six weeks of treatment with low dose IL-2 (9-18 MIU), once a day for five days a week (qd×5 d), followed by a one to four week "rest period" in which no IL-2 is administered and a subsequent treatment cycle that consists of six weeks of treatment with IL-2 at a dose of 9 MIU once a day for five days a week followed by a one to four week rest period in which no IL-2 is administered. In certain embodiments, the subsequent treatment cycle consisting of six weeks of treatment with IL-2 at a dose of 9 MIU once a day for five days a week followed by a one to four week rest period in which no IL-2 is administered, is repeated multiple times.

In a preferred embodiment, a patient having renal cell carcinoma is treated by first, administering a dose of 18 MIU of IL-2 per day for 5 days during one week; second, administering a dose of 9 MIU of IL-2 per day for 2 days followed by administering a dose of 18 MIU of IL-2 per day for 3 days during each week, repeated for 5 weeks; third, administering no IL-2 for 3 weeks; fourth, administering a dose of 9 MIU of IL-2 per day for 5 days of each week, repeated for 6 weeks; and fifth, administering no IL-2 for 3 weeks.

In certain embodiments, the IL-2 used for treatment of a patient having renal cell carcinoma is covalently conjugated to polyethylene glycol or polyoxyethylated polyol. In certain embodiments, a treatment cycle with IL-2, conjugated to polyethylene glycol or polyoxyethylated polyol, comprises administering 1-52 MIU of IL-2, every 5 days to 1 month, repeated for 1-24 weeks, followed by a rest period.

In certain embodiments, multiple cycles of treatment by any of the methods described herein are administered to a patient for a time period sufficient to effect at least a partial tumor response, for example, the time period may be at least 6 months or at least 12 months. Preferably, the time period is sufficient to effect a complete tumor response.

In certain embodiments, a patient having renal cell carcinoma is renally impaired (SCr>1.5 mg/dL), intolerant, or ineligible for treatment with high dose IL-2. Such a patient can be treated with low dose IL-2 by any of the methods described herein.

Where a subject undergoing therapy in accordance with the previously mentioned dosing regimens exhibits a partial response, or a relapse following a prolonged period of remission, subsequent courses of therapy may be needed to achieve complete remission of the disease. Thus, subsequent to a period of time off from a first treatment period, a subject may receive one or more additional treatment periods of IL-2 therapy. Such a period of time off between treatment periods is referred to herein as a time period of discontinuance. It is recognized that the length of the time period of discontinuance is dependent upon the degree of tumor response (i.e., complete versus partial) achieved with any prior treatment periods of therapy with IL-2.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Pharmaceutical Composition of IL-2 for Phase IV Human Clinical Trial

The IL-2 formulation used was manufactured by Chiron Corporation of Emeryville, Calif., under the tradename Proleukin®. The IL-2 in this formulation is a recombinantly produced, unglycosylated human IL-2 mutein, called aldesleukin, which differs from the native human IL-2 amino acid sequence in having the initial alanine residue eliminated and the cysteine residue at position 125 replaced by a serine residue (referred to as des-alanyl-1, serine-125 human interleukin-2). This IL-2 mutein is expressed in *E. coli*, and subsequently purified by diafiltration and cation exchange chromatography as described in U.S. Pat. No. 4,931,543, incorporated herein by reference in its entirety. The IL-2 formulation marketed as Proleukin® is supplied as a sterile, white to off-white preservative-free lyophilized powder in vials containing 1.3 mg of protein (22 MIU).

Example 2

Selection Criteria for Patients with Metastatic Renal Cell Carcinoma for Treatment with IL-2 in Phase IV Human Clinical Trial The following selection criteria were applied to patients with metastatic renal cell carcinoma:

Inclusion Criteria:

Patient has histologically documented renal cell carcinoma (clear cell, papillary, mixed or sarcomatoid tumors) with evidence of metastatic disease;

Patient has measurable or evaluable neoplastic disease which is determined within four weeks of entering the study;

Karnofsky Performance Status of patient is ≧60, corresponding to an Eastern Cooperative Oncology Group (ECOG) performance status (PS) of 0-2;

Patients must be greater than 18 years of age;

Patients should have adequate renal function as evidenced by a serum creatinine level of less than 1.8 mg/dl;

Hemoglobin >10 gm/dl; White blood cell≧4,000/ml; Platelet≧100,000/ml;

Normal thyroid stimulating hormone (TSH) level; and

Patient is willing and able to give written informed consent to participate in this study, including all required study procedures and follow-up visits.

Exclusion Criteria:

Patient has had previous treatment with Proleukin®;

Patients with active disease in the central nervous system detected on computerized tomography (CT) or magnetic resonance imaging (MRI) scan;

Patient has known hypersensitivity to any of the components of Proleukin®;

Patient is on concurrent clinical trials involving investigational agents, or patient has received investigational agents within the preceding four weeks;

Patient has had prior systemic therapy for renal cell carcinoma (patients who have undergone surgery for renal cell carcinoma are eligible for inclusion; patients who have undergone radiation therapy to a non-index lesion are eligible for study two weeks after completion of radiation);

Patient has New York Heart Association (NYHA) Class III or IV heart disease;

Patient has known autoimmune diseases, such as Crohn's disease;

Female patient is pregnant or lactating; and

Patient has metastatic disease with no evidence of disease following surgical resection of the metastases.

Example 3

Phase IV Clinical Study of Low Dose IL-2 Administered to Humans

Clinical Study Design and Objectives

The Phase IV clinical study of interleukin-2 in an alternative dose (ILIAD) was designed as a prospective, multi-center, single-arm, open-label study to evaluate the efficacy and safety of low dose Proleukin® administered subcutaneously in patients with metastatic renal cell carcinoma. The primary endpoint was an objective response rate (ORR)≧16%. Secondary endpoints included complete response (CR) and partial response (PR) rates, duration of response, progression free survival (PF), overall survival (OS), and incidence of adverse events (AEs). Participants included clinical investigators from both community and academic settings, with a preponderance of community clinicians. The ILIAD study screened 270 patients, of which 267 were enrolled.

Pretreatment evaluations included a complete history, physical exam, complete blood count (CBC), serum chemistry panel, thyroid stimulating hormone (TSH) level and appropriate radiographic studies to document sites of metastatic disease. Evaluations during treatment included a CBC, serum chemistry panel, TSH, and physical examination prior to the start of each new treatment cycle, a CBC prior to week four in each treatment cycle, and assessment of AEs at each patient contact. Prior to beginning each new treatment cycle after cycle 2, radiographic assessments of previously determined sites of metastatic disease were required. Case report forms documented evaluable areas of metastatic disease and the methods used to make such determinations.

ILIAD Treatment Regimen

All patients received Proleukin® on the following treatment schedule:

| Time Frame | Proleukin ® Treatment |
|---|---|
| Cycle 1, Week 1 | 18 MIU qd × 5 days |
| Cycle 1, Week 2-6 | 9 MIU qd × 2 days + 18 MIU qd × 3 days |
| Cycle 1, Week 7-9 | rest |
| Subsequent cycles wk 1-6 | 9 MIU qd × 5 days |
| Subsequent cycles wk 7-9 | rest |

Proleukin® was administered at 18 million international units (MIU)/day for 5 days (week 1, cycle 1), 9 MIU/day for 2 days followed by 18 MIU/day for 3 days (weeks 2-6, cycle 1), and 9 MIU/day for 5 days (weeks 1-6, cycles≧2). All treatment cycles were nine weeks in duration with six weeks on and three weeks off treatment. Duration of treatment was intended to continue for at least two cycles. Patients with progressive disease were removed from the study while responders could continue treatment at the investigator's discretion. Tumor response was evaluated every nine weeks until disease progression for up to two years. Patients were evaluated for survival at one and two years. The ILIAD intent-to-treat (ITT) population (n=263 patients) received at least one dose of study drug.

Dose modifications for toxicities were made according to guidelines stipulated in the protocol. Patients experiencing Grade 3 or higher toxicities had treatment withheld until symptoms resolved, and had subsequent doses reduced by half. If tolerated, a gradual dose escalation back to the specified protocol dose was implemented. The rate of dose escalation and the final dose were left to the discretion of the investigator. According to the protocol, any target dose should be low enough to allow the patient to receive Proleukin® as an outpatient, but high enough to ensure systemic absorption (in general this is in the range of 5-10 MIU/day by subcutaneous administration). Toxicities that persisted for more than two weeks resulted in the removal of that patient from the study.

Data for a total of 270 patients were collected. Three of the 270 patients were screen failures and 4 were enrolled but never dosed. The remaining 263 patients took at least one dose of study medication and were eligible for analyses (the Intent-to-treat Population). According to the dosing records of the 263 patients, 142 patients received two cycles of study drug (the Per-protocol Population). Sixty-five percent of Intent-to-treat patients and 70.4% of per-protocol patients withdrew due to disease progression or relapse.

Efficacy

After two cycles of treatment, patients were evaluated for progression or response by the investigator (see table below). The response categories were "complete response" (CR), "partial response" (PR), "progressive disease" (PD), "stable disease" (SD) and "undetermined" (UD).

Six of the 263 intent-to-treat patients (2.3%) were assessed as complete responders by the investigator and 12 (4.6%) as partial responders. Forty-eight intent-to-treat patients (18.3%) had stable disease and 156 (59.3%) had progressive disease status. Thirty-eight intent-to-treat patients (14.4%) were deemed undeterminable and 3 (1.1%) had missing assessments. The overall response rate (complete plus partial response) was 6.8% with a 95% confidence interval (CI) of 4.1-10.6%.

Six of the 142 per-protocol (i.e., received two cycles of study drug) patients (4.2%) were assessed as complete responders by the investigator and 11 (7.7%) as partial responders. The overall response rate (complete plus partial response) was 12.0% with a 95% confidence interval of 7.1-18.5%.

| Investigator Assessment of Best Response | | |
|---|---|---|
| | Intent-to-treat (N = 263) | Per-protocol (N = 142) |
| Complete Response | 6 (2.3%) | 6 (4.2%) |
| Partial Response | 12 (4.6%) | 11 (7.7%) |
| Stable Disease | 48 (18.3%) | 37 (26.1%) |
| Progressive Disease | 156 (59.3%) | 87 (61.3%) |
| Unable to Determine | 38 (14.4%) | 0 |
| Missing | 3 (1.1%) | 1 (0.7%) |
| Overall Response Rate (95% CI) | 6.8 (4.1-10.6) | 12.0 (7.1-18.5) |

Among the 263 intent-to-treat patients, 169 (64.3%) deaths occurred during the two year follow-up period. Among the 142 per-protocol patients, 73 (51.4%) deaths occurred. The following table summarizes the survival analysis results.

| Survival | | |
|---|---|---|
| | Intent-to-treat (N = 263) | Per-protocol (N = 142) |
| Number of Deaths | 169 (64.3%) | 73 (51.4%) |
| Median Survival in Years (95% C.I.) | 1.08 (0.97, 1.27) | 1.65 (1.39, 2.11) |
| One-year Survival Rate (95% C.I.) | 0.54 (0.48, 0.60) | 0.74 (0.67, 0.81) |
| Two-year Survival Rate (95% C.I.) | 0.32 (0.26, 0.38) | 0.45 (0.36, 0.55) |

Renal Function Subgroups

A subgroup analysis of the data from the ILIAD study was performed by comparing patients with normal renal function (serum creatinine (SCr)≦1.5 mg/dL) to patients with impaired renal function (SCr>1.5 mg/dL). A comparison of the normal and renally impaired subgroups show a similar frequency of nephrectomy (73 vs. 70%), PS=0 (28 vs. 23%), PS=1 (59 vs. 60%), and PS=2-3 (13 vs. 17%), respectively. See the table below.

|  | ILIAD (ITT) | ILIAD (SCr ≦ 1.5 mg/dL) | ILIAD (SCr > 1.5 mg/dL) |
|---|---|---|---|
| Evaluable patients | n = 263 | n = 209 | n = 53 |
| Nephrectomy, % | 72 | 73 | 70 |
| PS = 0, % | 27 | 28 | 23 |
| PS = 1, % | 59 | 59 | 60 |
| PS = 2-3, % | 14 | 13 | 17 |

Comparison of Efficacy for Patients with Normal and Impaired Renal Function

Figure 2:
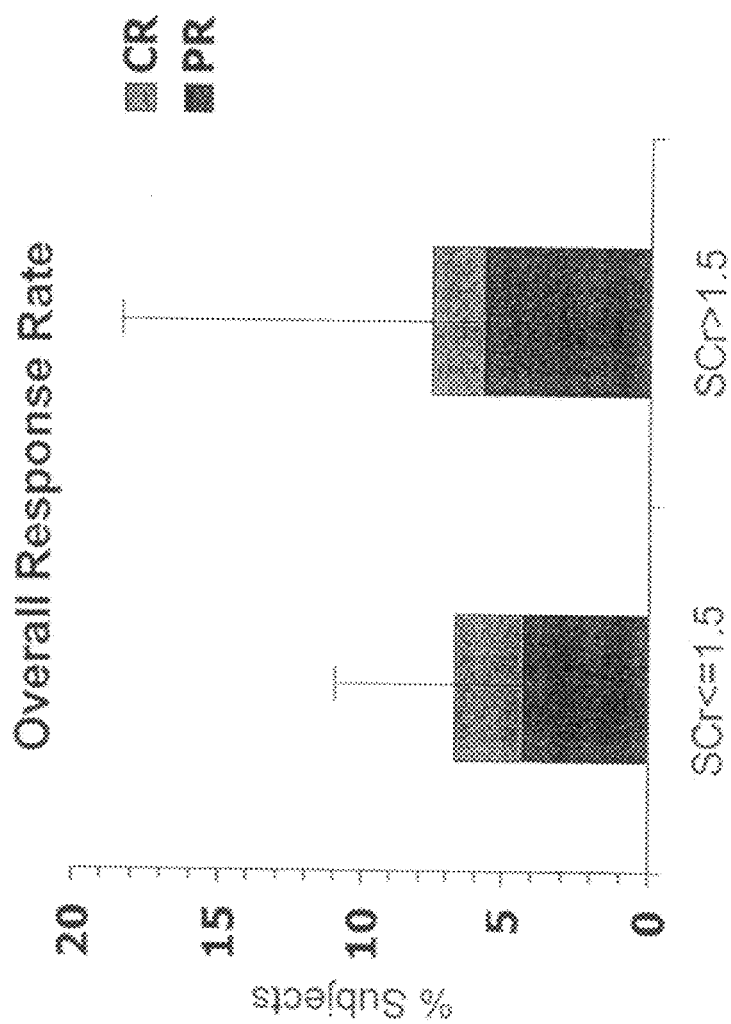
FIG. 2 shows a bar graph depicting the overall response rates for patients with metastatic renal cell carcinoma having normal (SCr≦1.5 mg/dL) and impaired renal function (SCr>1.5 mg/dL) treated with low dose IL-2 following the administration regimen described in Example 3. The percentage of subjects showing a complete response (CR) is shown with light shading. The percentage of subjects showing a partial response (PR) is shown with dark shading.
Figure 3:
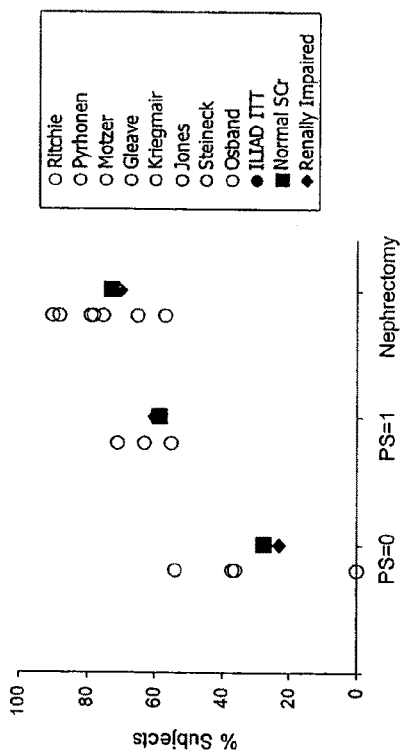
FIG. 3 compares the patient characteristics (PS, prior nephrectomy) of the population treated in the Phase IV clinical study of low dose IL-2 described herein to historical control groups. See Pyrhonen et al. (1999) J. Clin. Oncol. 17:2859-2867; Motzer et al. (1999) J. Clin. Oncol. 17:2530-40; Ritchie et al. (1999) Lancet 353:14-17; Kriegmair et al. (1995) Urology 45:758-762; and Jones et al. (1993) Cancer Biother. 8:275-288; Gleave et al (1998) New Engl. J. Med. 338:1265-1271; Steineck et al. (1990) Acta Oncol. 29:155-162; and Osband et al. (1990) Lancet 335:994-998 for a description of historical control groups from clinical studies of patients with renal cell carcinoma.

Patients with normal and impaired renal function were found to have similar outcomes. FIGS. 1-3 depict graphs comparing the relative efficacy of low dose IL-2 in patients with metastatic renal cell carcinoma having normal (serum creatinine (SCr)≦1.5 mg/dL) and impaired renal function (SCr>1.5 mg/dL) following the administration regimen described above. Compared to patients with normal renal function, renally impaired patients had similar or higher incidences of PR (5.7 vs. 4.3%), ORR (7.6 vs. 6.7%), median PFS (0.34 vs. 0.33 yrs), PFS-1 yr (28 vs. 18%), PFS-2 yr (16 vs. 10%), and OS-2 yr (39 vs. 31%). CR (1.9 vs. 2.4%). Median survival (1.0 vs. 1.1 yrs) and OS-1 yr (52 vs. 55%) were slightly lower for the renally impaired subgroup. See the table below for a comparison of the efficacy of treatment for the renal subgroups.

|  | ILIAD (ITT) | ILIAD (SCr ≦ 1.5 mg/dL) | ILIAD (SCr > 1.5 mg/dL) |
|---|---|---|---|
| Evaluable patients | n = 263 | n = 209 | n = 53 |
| CR % | 2.3 | 2.4 | 1.9 |
| PR % | 4.6 | 4.3 | 5.7 |
| ORR % | 6.8 (4.1-10.6) | 6.7 (3.7-11.0) | 7.6 (2.1-18.2) |
| Mean duration of response, yrs | 1.7 (1.1-1.9) | 1.5 (1.0-1.7) | NE |
| Median PFS, yrs | 0.33 (0.31-0.34) | 0.33 (0.30-0.34) | 0.34 (0.28-0.66) |
| PFS 1 yr, % | 20 (15-25) | 18 | 28 |
| PFS-2 yr, % | 11 (7-15) | 10 | 16 |
| Median survival time, yrs | 1.1 (1.0-1.3) | 1.1 (0.9-1.3) | 1.0 (0.9-2.5) |
| OS-1 yr, % | 54 (48-60) | 55 | 52 |
| OS-2 yr, % | 32 (26-38) | 31 | 39 |

When renal subgroups were controlled for prior nephrectomy and performance status, PFS, and OS remained comparable. Univariate unconditional logistic regression models were generated using standard SAS programs to estimate odds ratios and Wald 95% confidence intervals for ORR. For renally impaired patients, ORR was numerically lower than for patients with normal renal function when subgroups were controlled for nephrectomy (odds ratio=0.52), PS=0 (odds ratio=0.57), and PS=1 (odds ratio=0.63). However, these differences were not statistically significant and should be interpreted with caution due to the small number of responders in the normal (n=14) and impaired (n=4) renal function subgroups. Cox proportional hazards regression models were used to obtain hazard ratios and 95% confidence intervals for PFS and OS. PFS for renally impaired patients was similar to that of patients with normal renal function when the subgroups were controlled for nephrectomy (hazard ratio=0.86), non-nephrectomy (hazard ratio=1.09), PS=0 (hazard ratio=1.15), and PS=1 (hazard ratio=0.71). Survival for renally impaired patients was also similar to that of patients with normal renal function when the subgroups were controlled for nephrectomy (hazard ratio=0.92), non-nephrectomy (hazard ratio=1.03), PS=0 (hazard ratio=1.11), and PS=1 (hazard ratio=0.82). See table below.

| Univariate Evaluation of ILIAD Subgroups (SCr > 1.5 vs. ≦1.5 mg/dL) | | | |
|---|---|---|---|
| ORR | Odds Ratio | 95% Wald CI | No. of patients |
| Nephrectomy | 0.52 | 0.11-2.39 | 189 |
| Non-nephrectomy | NE | NE | 73 |
| PS = 0 | 0.57 | 0.06-5.02 | 70 |
| PS = 1 | 0.63 | 0.07-5.42 | 155 |
| PFS | Hazard Ratio | 95% CI | No. of patients |
| Nephrectomy | 0.86 | 0.58-1.27 | 189 |
| Non-nephrectomy | 1.09 | 0.61-1.93 | 73 |
| PS = 0 | 1.15 | 0.58-2.29 | 70 |
| PS = 1 | 0.71 | 0.47-1.07 | 155 |
| OS | Hazard Ratio | 95% CI | No. of patients |
| Nephrectomy | 0.92 | 0.58-1.46 | 189 |
| Non-nephrectomy | 1.03 | 0.54-1.95 | 73 |
| PS = 0 | 1.11 | 0.46-2.68 | 70 |
| PS = 1 | 0.82 | 0.51-1.31 | 155 |

NE = Not estimable

Comparison to Historical Controls

A literature search identified eight publications that used placebo or pseudo-placebo control groups in studies of renal cell carcinoma patients not previously treated with immunotherapy (Pyrhonen et al. (1999) J. Clin. Oncol. 17:2859-2867; Motzer et al. (1999) J. Clin. Oncol. 17:2530-40; Ritchie et al. (1999) Lancet 353:14-17; Kriegmair et al. (1995) Urology 45:758-762; and Jones et al. (1993) Cancer Biother. 8:275-288; Gleave et al (1998) New Engl. J. Med. 338:1265-1271; Steineck et al. (1990) Acta Oncol. 29:155-162; Osband et al. (1990) Lancet 335:994-998). Results for control groups in these published studies varied greatly, most likely due to differences in control treatment (none, hormonal, or chemotherapy), study design, patient selection criteria, and prior patient treatment. See Table below.

| Historical Control Data | | | | | | | | |
|---|---|---|---|---|---|---|---|---|
|  | Ritchie 1999 | Pyrhonen 1999 | Motzer 1999 | Gleave 1998 | Kriegmair 1995 | Jones 1993 | Steineck 1990 | Osband 1990 |
| Evaluable patients | n = 168 | n = 81 | n = 274 | n = 90 | n = 35 | n = 377 | n = 30 | n = 45 |
| Control | MPA | VLB | Chemo or hormonal | placebo | MPA | Chemo | MPA | CIM |

-continued

Historical Control Data

|  | Ritchie 1999 | Pyrhonen 1999 | Motzer 1999 | Gleave 1998 | Kriegmair 1995 | Jones 1993 | Steineck 1990 | Osband 1990 |
|---|---|---|---|---|---|---|---|---|
| PS = 0 | UK | UK | 0 | 36 | UK | 37 | UK | 54 |
| PS = 1 | UK | UK | 71 | 55 | mean | 63 | UK | UK |
| PS ≧ 2 | UK | UK | 29 | 9 | UK | 0 | UK | UK |
| Nephrectomy % | 57 | 88 | 65 | 78 | UK | 79 | 90 | 75 |
| Median age | 55-65 | 62 [39-77] | 58 [18-82] | 62 | 66 [47-79] | 58 [22-82] | 62 [40-77] | 63 (34-84) |
| CR % | 0 | 1.2 | UK | 3.3 | 0 | 0.80 | 3.3 (0-17) | 0 |
| PR % | 7.1 | 1.2 | UK | 3.3 | 0 | 4.2 | 0 | 4.8 |
| ORR % | 7.1 | 2.4 | UK | 6.6 (2.7-14.5) | 0 | 5.0 (3-7) | 3.3 (0-17) | 4.8 |
| Median PFS, yrs | 0.25 | 0.17 | UK | 0.16 (0.14-0.32) | UK | UK | UK | UK |
| PFS 1 yr, % | 10 | 4.1 | UK | 4.0 | UK | UK | UK | UK |
| PFS-2 yr, % | 1.1 | 4.1 | UK | NE | UK | UK | UK | UK |
| Median survival time, yrs | 0.54 | 0.73 | 0.53 (0.43-0.63) | 1.3 (0.5-1.5) | 0.83 | 0.63 | 0.58 | 0.73 |
| OS-1 yr, % | 31 | 38 | UK | 54 | 30 | 32 | 26 | 45 |
| OS-2 yr, % | 12 | 19 | UK | 9 | 20 | 11 | 16 | NE |

Figure 4:
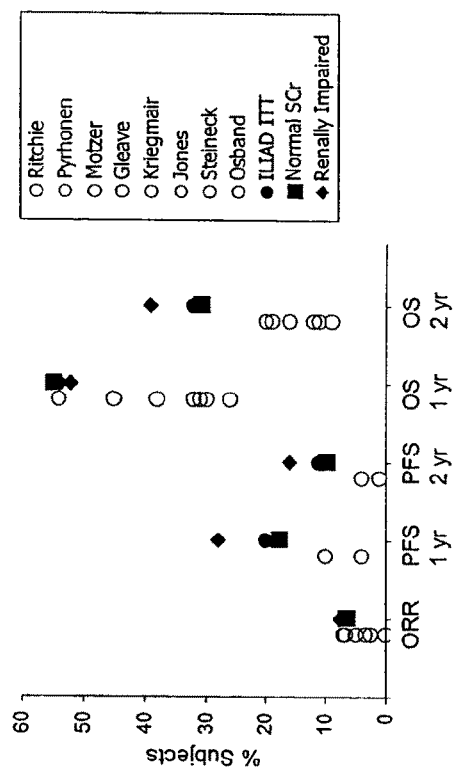
FIG. 4 compares the patient outcomes (ORR, PFS, OS at 1 year, OS at 2 years) of the population treated in the Phase IV clinical study of low dose IL-2 described herein to historical control groups.

95% CI is given in parenthesis ranges are given in brackets
UK = unknown,
NE = Not estimable
MPA = medroxyprogesterone,
VLB = vinblastine,
CIM = cimetidine Outcomes for the normal renal function subgroup, impaired renal function subgroup, and ILIAD ITT population were more favorable than most of the measured outcomes in the historical control groups. The percentage of patients with PS=0, PS=1, and prior nephrectomy for the ILIAD renal subgroups and ITT population were near the median of the range for the historical control groups, suggesting that the ILIAD patient population is comparable to that of the historical controls (see FIG. 3). In contrast, the ILIAD ITT population and renal subgroups were numerically more favorable than historical controls for a majority (43/50, 86%) of the efficacy outcomes (see FIG. 4). Results for the renal subgroups and ITT population were the same or numerically lower compared to 7/50 (14%) of the efficacy outcomes from historical controls: CR in the Steineck (1990) study; PR in the Osband (1990) study; PR and ORR in the Ritchie (1999) study; and CR, median survival and OS-1 yr in the Gleave (1998) study. When compared by endpoints, the ILIAD study was more favorable than historical controls for a majority of response (16/21, 76%), PFS (8/8, 100%), and survival (19/21, 90%) outcomes.

Figure 5:
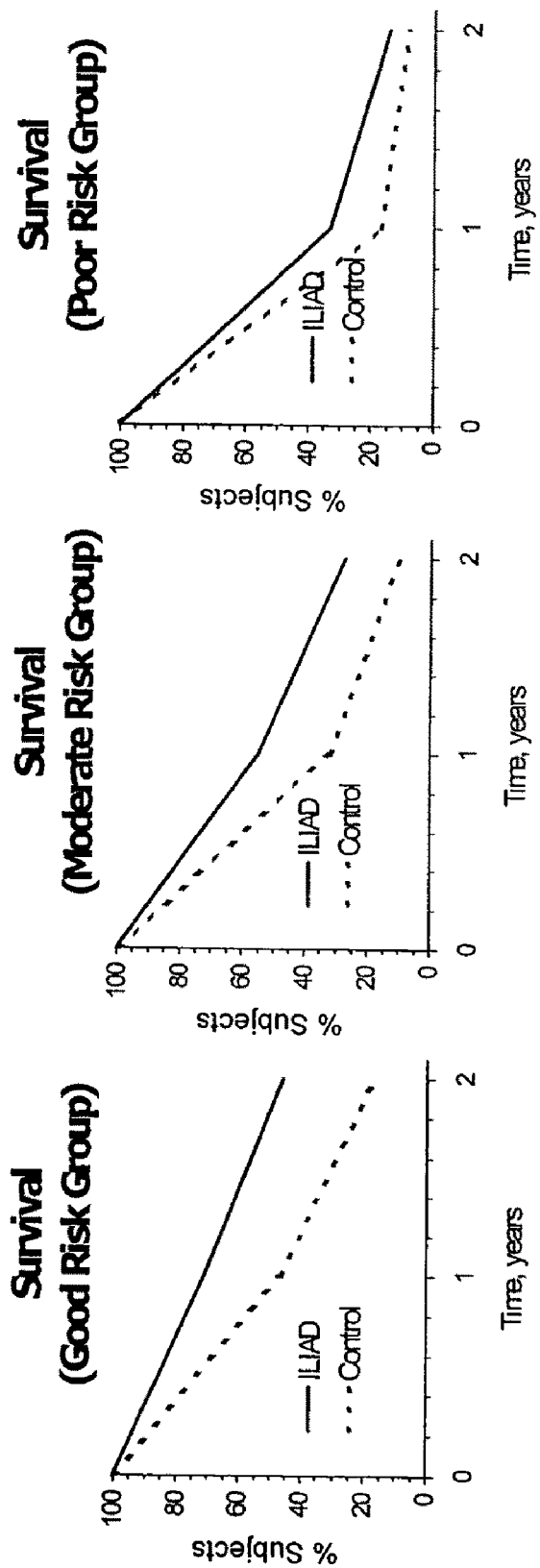
FIG. 5 compares the survival rate of patients treated with low dose IL-2 following the administration regimen described in Example 3 to that of a historical control group of patients treated with chemotherapy instead of IL-2 (Jones et al. (1993) J. Clin. Oncol. 12:2714-2722). Patients were subdivided into risk groups according to the Jones system of risk factor stratification as follows: Good Risk (0-1 risk factors), Moderate Risk (2 risk factors), and Poor Prognosis (all 3 risk factors).

In addition, ILIAD patients stratified by risk groups had a higher survival rate than historical controls. The survival rate of patients treated with low dose IL-2 was compared to that of a historical control group (described in Jones et al., supra) of patients treated with chemotherapy instead of IL-2. Patients were subdivided into risk groups according to the Jones system of risk factor stratification, which is based on a combination of identified risk factors: ECOG PS>1, time from diagnosis to treatment<2 years, and metastases at more than one site. Patients were subdivided into the following Jones Risk groups: Good Risk (0-1 risk factors), Moderate Risk (2 risk factors), and Poor Prognosis (all 3 risk factors). FIG. 5 shows separate plots of the percentage of surviving subjects versus time in years for each of the risk groups. Patients treated with low dose IL-2 according to the regimen described in Example 3 had a numerically higher survival rate in all three Jones Risk groups compared to historical controls. However, the difference in survival between the ILIAD patients and historical controls appears to decrease as the risk groups become less favorable. See table below.

| Risk Group | ILIAD (Good) | Control (Good) | ILIAD (Moderate) | Control (Moderate) | ILIAD (Poor) | Control (Poor) |
|---|---|---|---|---|---|---|
| Evaluable patients | n = 70 | n = 118 | n = 125 | n = 140 | n = 63 | n = 94 |
| Median survival time, yrs | 2.0 (1.3-2.2) | 0.96 | 1.1 (0.93-1.5) | 0.55 | 0.61 (0.46-0.80) | 0.43 |
| OS-1 yr, % | 71 (60-82) | 46 | 55 (46-64) | 27 | 33 (21-45) | 14 |
| OS-2 yr, % | 47 (34-61) | 17 | 32 (22-41) | 10 | 17 (7-28) | 8 |

95% CI is given in parenthesis

Toxicity

Adverse events were determined to be "not related", "possibly related" or "probably related" to study treatment by the investigator. The most frequently occurring adverse effect was fatigue (41.1% of patients), followed by rigors (36.9%), nausea (36.5%), pyrexia (32.7%), vomiting NOS (22.1%) and anorexia (20.9%). The following treatment-related adverse events were observed in at least 10% of patients (see table below):

| Preferred Term | Intent-to-treat (N = 263) Patients (%) |
|---|---|
| Fatigue | 108 (41.1) |
| Rigors | 97 (36.9) |
| Nausea | 96 (36.5) |
| Pyrexia | 86 (32.7) |
| Vomiting NOS | 58 (22.1) |
| Anorexia | 55 (20.9) |
| Diarrhoea NOS | 49 (18.6) |
| Injection site reaction NOS | 48 (18.3) |
| Dermatitis NOS | 41 (15.6) |
| Myalgia | 28 (10.6) |

Low dose Proleukin® therapy is less nephrotoxic than high dose Proleukin®. High dose Proleukin® therapy has been shown to cause significant renal toxicity, as measured by mean peak SCr>4 mg/dL in the first cycle of treatment and >6 mg/dL during the second cycle of therapy for patients with elevated SCr at baseline (Belldegrun et al. 1987). A smaller, but still dramatic increase in mean peak SCr (up to 3 mg/dL) was observed for patients with normal SCr at baseline. SCr levels returned to baseline within 30 days for 60% of patients with impaired renal function compared to 98% of patients with normal renal function. These results suggest that high dose Proleukin® produces higher nephrotoxicity in renally impaired patients than in patients with normal renal function. In contrast, low dose Proleukin® produced only small increases in SCr during treatment (generally<2 mg/dL), that were comparable between the normal and impaired renal function subgroups. Elevations in SCr>3 mg/dL were rare for either subgroup. Patients with SCr excursions in this range (<3 mg/dL) would not be expected to have severe symptoms or specific treatment requirements.

The frequency and grade of adverse events (AEs) were generally comparable between subgroups of patients with normal and impaired renal function. Compared to the normal subgroup, the renally impaired subgroup had a slightly lower number of total serious adverse events (SAEs) (26 vs. 30%), AEs (77 vs. 89%), and drug-related AEs (76 vs. 81%). The number of AEs leading to discontinuation was slightly higher in the renally impaired subgroup (30 vs. 25%). In both the normal and renally impaired subgroups, the highest percentage of AEs were Grade 3 (42 vs. 34%), followed by Grade 2 (33 vs. 23%), Grade 4 (9 vs. 13), Grade 1 (4 vs. 8%), and Grade 5 (1 vs. 0%), respectively.

The most common adverse events (reported in >10% of patients in either subgroup) were generally comparable between the normal and renally impaired subgroups and included fatigue (43 vs. 45%), rigors (38 vs. 36%), pyrexia (39 vs. 23%), injection site reaction (18 vs. 21%), nausea (39 vs. 36%), vomiting (25 vs. 19%), diarrhea (20 vs. 19%), dermatitis NOS (18 vs. 11%), anorexia (23 vs. 19%), cough (20 vs. 9%), dyspnea NOS (13 vs. 26%), insomnia (9 vs. 17%), arthralgia (12 vs. 13%), myalgia (11 vs. 9%), lower limb oedema (8 vs. 17%), reduced weight (11 vs. 4%), and hypotension NOS (6 vs. 11%), respectively.

LD Proleukin® nephrotoxicity was similar between renal subgroups. Nephrotoxicity of LD Proleukin® therapy was evaluated by comparing SCr levels during each treatment cycle to baseline measurements. Although peak SCr levels increased slightly during treatment for a large number of patients, peak SCr>2.0 mg/dL was observed in only five patients in the renally impaired subgroup and eight patients in the normal renal function subgroup. Peak SCr>3.0 mg/dL was uncommon and observed in only one patient in the renally impaired subgroup and two patients in the normal renal function subgroup.

Conclusion

Low-dose interleukin-2 appears to be safe and effective for treating renally impaired patients with metastatic renal cell carcinoma, who are ineligible for high-dose IL-2 therapy. The results of the Phase IV clinical study indicate that low dose Proleukin® produces similar response rates, progression free survival (PFS), and overall survival (OS) in both normal and renally impaired patients. Efficacy outcomes for normal and renally impaired patients treated with low dose Proleukin® were generally higher than that reported for historical control groups. Nephrotoxicity with low dose Proleukin® was similar between the renal subgroups, and dramatically lower than that observed with high dose Proleukin® in renally impaired patients.

Example 4

Treatment of Metastatic Renal Cell Carcinoma by Administration of Low Dose IL-2

An IL-2 formulation is administered to patients with a histologic diagnosis of metastatic renal cell carcinoma. The concentration of IL-2 in the formulation is about 22 MIU. The IL-2 formulation is administered by subcutaneous injection. The treatment comprises two 9-week cycles. The first cycle comprises six weeks of treatment with low dose IL-2 at 9-18 MIU, once a day for five days a week (qd×5 d), followed by a three week rest period. The second cycle comprises six weeks of treatment with low dose IL-2 at 9 MIU, once a day for five days a week (qd×5 d), followed by a three week rest period. Cycles of treatment are repeated in responding patients.

While the preferred embodiments of the invention have been illustrated and described, it will be appreciated that various changes can be made therein without departing from the spirit and scope of the invention.

What is claimed is:

1. A method for treating a human patient having renal cell carcinoma, the method comprising:
   a) first, administering a dose of 18 MIU of an IL-2 mutein per day for 5 days during one week;
   b) second, administering a dose of 9 MIU of the IL-2 mutein per day for 2 days followed by administering a dose of 18 MIU of the IL-2 mutein per day for 3 days during each week, repeated for 5 weeks;
   c) third, administering no IL-2 mutein for 3 weeks;
   d) fourth, administering a dose of 9 MIU of the IL-2 mutein per day for 5 days of each week, repeated for 6 weeks; and
   e) fifth, administering no IL-2 mutein for 3 weeks,
   wherein said IL-2 mutein is administered by subcutaneous, intraperitoneal, intramuscular, intravenous, oral, pulmonary, nasal, topical, or transdermal administration, or by infusion or suppositories.

2. The method of claim 1, wherein said IL-2 mutein is recombinantly produced IL-2 comprising an amino acid sequence having at least 70% sequence identity to the amino acid sequence of human IL-2.

3. The method of claim 1, wherein said IL-2 mutein comprises an amino acid sequence having at least 80% sequence identity to the amino acid sequence of human IL-2.

4. The method of claim 1, wherein said IL-2 mutein comprises an amino acid sequence having at least 90% sequence identity to the amino acid sequence of human IL-2.

5. The method of claim 1, wherein said IL-2 mutein comprises an amino acid sequence having at least 95% sequence identity to the amino acid sequence of human IL-2.

6. The method of claim 1, wherein said IL-2 mutein is des-alanyl-1, serine-125 human interleukin-2 (aldesleukin).

7. The method of claim 1, wherein said renal cell carcinoma is metastatic.

8. The method of claim 1, wherein multiple cycles of the method of treatment are administered to said subject for a time period sufficient to effect at least a partial tumor response.

9. The method of claim 1, further comprising multiple cycles of a treatment comprising:
   a) administering a dose of 9 MIU of the IL-2 mutein per day, in 1-3 doses a day, for 3-6 days a week, repeated for 1-24 weeks; and
   b) administering no IL-2 mutein for 1-4 weeks;
   administered to said subject for a time period sufficient to effect at least a partial tumor response.

10. The method of claim 8, wherein the time period is at least 6 months.

11. The method of claim 9, wherein the time period is at least 6 months.

12. The method of claim 8, wherein the time period is at least 12 months.

13. The method of claim 9, wherein the time period is at least 12 months.

14. The method of claim 8, wherein a complete tumor response is effected.

15. The method of claim 9, wherein a complete tumor response is effected.

16. The method of claim 1, wherein said IL-2 mutein is administered subcutaneously.

17. The method of claim 1, wherein said patient is renally impaired.

18. The method of claim 1, wherein said patient is intolerant of high dose IL-2 treatment.

* * * * *

SEQUENCE LISTING

<160> NUMBER OF SEQ ID NOS: 1

<210> SEQ ID NO 1
<211> LENGTH: 133
<212> TYPE: PRT

```
<213> ORGANISM: Homo sapiens

<400> SEQUENCE: 1

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
            130
```